United States Patent [19]

Varlerberghe et al.

[11] 4,013,787

[45] * Mar. 22, 1977

[54] PIPERAZINE BASED POLYMER AND HAIR TREATING COMPOSITION CONTAINING THE SAME

[75] Inventors: Guy Varlerberghe, Montjay-la-Tour par Claye-Souilly; Henri Sebag, Paris, both of France

[73] Assignee: Societe Anonyme dite: L'Oreal, Paris, France

[ * ] Notice: The portion of the term of this patent subsequent to Nov. 4, 1992, has been disclaimed.

[22] Filed: July 29, 1975

[21] Appl. No.: 600,188

Related U.S. Application Data

[63] Continuation-in-part of Ser. No. 310,088, Nov. 28, 1972, Pat. No. 3,917,817.

[30] Foreign Application Priority Data

Nov. 29, 1971 Luxembourg .......................... 64371
Aug. 2, 1974 France .......................... 74.27030

[52] U.S. Cl. .......................... 424/70; 252/DIG. 2; 252/DIG. 3; 252/DIG. 13; 252/542; 252/544; 252/545; 252/547; 252/548; 252/550; 252/551; 260/2 BP; 260/268 PL; 424/DIG. 1; 424/DIG. 2; 424/DIG. 4; 424/47; 424/71

[51] Int. Cl.$^2$ .......................... A61K 7/06
[58] Field of Search .......................... 424/DIG. 1, DIG. 2, 424/70, 71, 47; 260/2 BP, 268 PL; 252/DIG.2, DIG. 3, DIG. 13

[56] References Cited

UNITED STATES PATENTS

| | | | |
|---|---|---|---|
| 3,069,390 | 12/1962 | Kline et al. | 424/47 X |
| 3,250,682 | 5/1966 | Wilmsmann et al. | 424/71 |
| 3,267,046 | 8/1966 | Bonvinci | 260/2 BP |
| 3,274,312 | 9/1966 | Compostella et al. | 264/78 |
| 3,280,044 | 10/1966 | Bonvinci | 260/2 BP |

*Primary Examiner*—Albert T. Meyers
*Assistant Examiner*—Vera C. Clarke
*Attorney, Agent, or Firm*—Cushman, Darby & Cushman

[57] ABSTRACT

Piperazine-based low molecular weight film-forming cationic polymer is employed in a cosmetic hair-conditioner composition comprising a solution of the polymer in amounts of about 0.1–5 weight percent of the composition in a solvent such as water, acidified water, or aqueous alcohol solution.

20 Claims, No Drawings

PIPERAZINE BASED POLYMER AND HAIR TREATING COMPOSITION CONTAINING THE SAME

This application is a continuation-in-part of our application Ser. No. 310,088 filed Nov. 28, 1972, now U.S. Pat. No. 3,917,817.

The present invention relates to compositions for treating and conditioning the hair. More particularly, the present invention relates to cosmetic compositions for the living human hair, containing a low molecular weight, film-forming cationic polymer.

Many people's hair, because of its general state or its sensitivity due to relatively frequent periodic treatments such as bleaching, dyeing or permanent waving, often is difficult to comb out and to arrange especially in the case of abundant hair. To varying degrees, such hair often is also dry, dull and rough or lacks vigor and life. Further, such hair is very sensitive to humidity in the air, which explains why hair-sets do not hold for an acceptable length of time. Consequently, the frequency of such treatments, as described above, has to be increased, which, in turn, increases the above-mentioned disadvantages.

The present invention now makes it possible to substantially limit or avoid these disadvantages by applying to the hair as a conditioner therefor a low molecular weight, film-forming cationic polymer that imparts to the hair an appearance of vigor and radiance.

In accordance with a first embodiment of this invention, this polymer which imparts to the hair an appearance of vigor and radiance can be used alone or as the main component in a hair-dressing lotion, cream, gel, hair-setting lotion, hair-setting reinforcer, or alternatively, as an adjuvant in a composition for shampooing, setting, in permanent waving the hair, in a hair dyeing composition, in a cream for treating dry or greasy hair, in an anti-dandruff lotion or in similar compositions for application to the hair.

The application of the hair conditioner cosmetic composition of this first embodiment of the present invention results in improving the facility and ease of combing out wet hair and imparts thereto brilliancy, softness and manageability of dry hair. Hair treated with this composition feels lighter, while at the same time appears thicker and more alive.

The conditioner according to the first embodiment of this invention, which acts as a softener and emollient, produces after application of the same to the hair in a shampoo, for example, a more brilliant, more voluminous and more aerated hair without the appearance of static electricity. Further, this phenomenon polymer provides the additional advantage of avoiding a powdering phenomemon which is frequently observed with numerous conventionally employed polymers. Moreover, the inclusion of this hair conditioner in cosmetic compositions for the hair, which compositions also include other components or hair treating agents, does not entail any appreciable reduction of the properties or effectiveness of these other components.

The cationic polymer of this first embodiment of the present invention is characterized by the fact that the cationic groups are part of the main polymer chain and that they are essentially derived from bisecondary heterocyclic amines, preferably, piperazine. Structurally, the low molecular weight, film-forming, cationic polymer of the first embodiment can be represented by the pattern $$- A - Z - A - Z - A - Z - \quad (I)$$

wherein A represents a radical derived from a heterocycle containing two secondary amine functions and, preferably, the radical

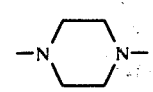

and Z represents the symbol B or B', each of which independently represents a bivalent radical selected from the group consisting of (i) hydroxypropylene, (ii) alkylene having up to 5 carbon atoms inclusive and interrupted by 1 - 2 members selected from the group consisting of —CONH,

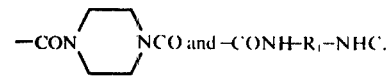

wherein $R_1$ represents an alkylene radical having up to 6 carbon atoms, preferably isopropylidene, and (iii) hydroxy alkylene wherein the alkylene moiety has up to 6 carbon atoms inclusive and is interrupted by a member selected from the group consisting of alkylamine wherein the alkyl moiety has 8 to 18 carbon atoms, benzylamine, oleylamine and oxygen.

Often, polymers of the present invention are those in which A has the meaning given above and B and B' each independently represent a branched or straight chain radical selected from the group consisting of hydroxyalkylene having 1–6 and, preferably, 3 carbon atoms, lower alkyl-carbonamide-lower alkyl-carbonamide-lower alkyl having 4 to 9 and, preferably, 6 to 7 carbon atoms, hydroxypropyl-oxyhydroxypropyl, hydroxypropyl-alkylamino-hydroxypropyl wherein the alkyl moiety has 8 to 18 carbon atoms, hydroxypropyl-alkenylamino-hydroxypropyl wherein the alkenyl moiety has 18 carbon atoms, hydroxypropyl-piperazinyl-hydroxypropyl, propionyl-piperazinyl-propionyl and hydroxypropyl-benzylamino-hydroxypropyl.

The polymers of the present invention are more generally strictly alternated, i.e. of the type $$- A - B - A - B - A - B - \quad (II)$$

wherein A and B have the meanings given above.

These rigorously alternated polymers, which can be used in the present invention, can be prepared by conventional processes such as by polyaddition or polycondensation of (a) piperazine or a derivative thereof such as, for example, N,N' bis(hydroxyethyl)piperazine, N,N'-bis(2,3 epoxypropyl)piperazine, 1,3-piperazine-2-propanol and N,N'-bis(chloracetyl)piperazine on (b) a bifunctional compound such as (1) alkyl or alkyl-aryl dihalides, such as ethylene chloride, ethylene bromide or bis chloromethyl 1,4-benzene wherein the alkyl moiety has 1–4 carbon atoms, the aryl moiety is phenyl and the halide moiety is chloride or bromide;

(2) more complex dihalogen derivatives, such as bis (chloroacetyl) ethylene diamine;

(3) bis halohydrins, such as bis 3-chloro 2-hydroxy propyl ether, or other bis chlorohydrins which can be obtained by conventional procedures such as by the condensation of epichlorohydrin on (i) a primary amine, optionally hydroxylated, (ii) on a bisecondary diamine such as piperazine, 4,4'-dipiperidyl, bis 4,4' (N-methylamino-phenyl) methane, N,N'-dimethylethylene diamine or propylene diamine, (iii) on a α,ω-dimercaptoalkane, (iv) on a diol such as ethylene glycol or (v) on a bis phenol such as hydroquinone or "bis phenol A;"

(4) bis epoxide such as diglycidyl ether or N,N' bis (epoxy-2,3 propyl) piperazine, eventually obtained from the corresponding bis halohydrin;

(5) epihalohydrins, such as epichlorohydrin or epibromohydrin;

(6) bis unsaturated derivatives, such as divinyl sulfone, bis maleimide derived from ethylene diamine, or bis acrylamide such as methylene bis acrylamide or piperazine bis acrylamide or isopropylidene bis acrylamide derived from biprimary or bisecondary diamines;

(7) unsaturated acids, such as acrylic or methacrylic acid or their methyl or ethyl esters;

(8) diacids, such as succinic, adipic, 2,2,4-trimethyl or 2,4,4-trimethyl adipic or terephthalic acids, acid chlorides or the corresponding methyl or ethyl esters;

(9) diisocyanates, such as toluene diisocyanate or 2,2,4- or 2,4,4-trimethyl hexamethylene isocyanate.

The polyaddition or polycondensation reaction can be carried out at ambient pressure and at a temperature ranging from about 0° to 100° C, the molar ratio of (a) to (b), defined above, being 0.85 : 1 to 1.15 : 1.

Of course, the polymers of the present invention can in certain cases advantageously be prepared in essentially the same way by polycondensation or polyaddition of (a') N,N'bis(3-chloro 2-hydroxy propyl) piperazine or N,N'bis(2,3-epoxy propyl) piperazine or N,N'-bis(chloroacetyl) piperazine on (b') a bifunctional compound such as a bisecondary diamine, a dimercaptan, a diol, a diphenol, a diacid, and a primary amine such as an alkylamine, alkenylamine, aralkylamine, of which the two hydrogen atoms can be substituted and which behaves as a bifunctional compound, the molar ratio of (a') to (b') ranging from 0.85 : 1 to 1.15 : 1.

Further, the cationic polymers of the present invention can also, in certain cases, be of the pattern $$— A — B — A — B' —$$ (III)

i.e. be made up of polymer chains in which A, representing a bisecondary heterocyclic amine group, for example, the piperazine group is distributed regularly, the two B and B' groups designated by Z in formula (I) being distributed statistically. This type of polymer is obtained when piperazine or one of its derivatives is condensed with a mixture of two bifunctional derivatives.

The polycondensates of type I, II or III can then, in accordance with conventional procedures, be oxidized with hydrogen peroxide or with peracids, or alternatively can be quaternized with known quaternization agents such as, for example, the chloride, bromide, iodide, sulfate, mesylate or tosylate of lower alkyl and preferably of methyl or ethyl, benzyl chloride or bromide or they can be condensed with ethylene oxide, propylene oxide, epichlorohydrin or glycidol.

In those polymers of this invention wherein Z or B and B' groups do not comprise base nitrogen or thioether, only the A groups will be modified statistically or almost totally by quaternization or oxidation. Otherwise, any group can be modified.

The oxidation reaction of the polycondensate of type I, II or III can be performed with the amount of oxidizing agent being present in amounts from 0 to 100% relative to the oxidizable groups, while the quaternization reaction of the polycondensate of type I, II or III can be performed with the amount of quaternization agent being present in amounts of 0 to 50%.

The cationic polymers of the present invention are also characterized by the fact that they are all film-forming and are generally of relatively low molecular weight, i.e. less than 15,000 and generally about 1,000 – 15,000. They are water soluble in acid medium and a number of them are also soluble as such in water without addition of acid or in dilute alcohol medium such as ethanol or isopropanol. The alcohol, i.e. lower alkanol, can be present in amounts of about 0 to 50 percent by weight of said composition. Generally, when an aqueous acidic medium is employed as the solvent for the polymers of the present invention, the acid employed can be hydrochloric, acetic, lactic, or tartaric acid in amounts sufficient to solubilize the said polymer. Generally, the acid will be present in amounts of about 0 to 5 percent by weight of the composition. These polymers are particularly effective for hair which has become sensitive as a result of such treatments as bleaching, permanent waving, or dyeing. They can, however, also advantageously be used for normal hair.

Thus, an object of the present invention is the provision of a cosmetic composition for conditioning the hair comprising a solution in a solvent selected from the group consisting of water and an aqueous solution of a lower alkanol, of a member selected from the group consisting of (1) a low molecular weight, film-forming, cationic polymer of the formula $$— A — Z — A — Z — A — Z —$$ (I)

in which A represents a radical derived from a heterocycle carrying two secondary amine functions and preferably the radical

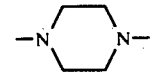

and Z represents the symbol B or B'; B and B' each independently representing a bivalent radical selected from the group consisting of (i) hydroxypropylene, (ii) alkylene having up to 5 carbon atoms inclusive and interrupted by 1–2 members selected from the group consisting of $CONH_1$

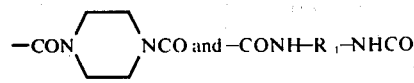

wherein $R_1$ represents an alkylene having up to 6 carbon atoms and preferably an isopropylidene radical and (iii) hydroxy alkylene wherein the alkylene moiety has up to 6 carbon atoms inclusive and interrupted by a member selected from the group consisting of alkylamine wherein the alkyl moiety has 8–18 carbon atoms, benzylamine, oleylamine and oxygen, or (2) quaternary ammonium salt of the cationic polymer in (1) or (3) the oxidation product of the cationic polymer in (1).

Many of the polymers of formula (1) are new compounds.

Among the preferred polymers are those in which A is

and B and B', each independently represent a branched or straight chain radical selected from the group consisting of hydroxyalkylene having 1–6 carbon atoms, preferably 3 carbon atoms, lower alkyl-carbonamide-lower alkyl-carbonamide-lower alkyl having 4–9 and preferably 6–7 carbon atoms, hydroxypropyl-oxyhydroxypropyl, hydroxypropyl-alkylamino-hydroxypropyl wherein the alkyl moiety has 8–18 carbon atoms, hydroxypropyl-alkenylamino-hydroxypropyl wherein the alkenyl moiety has 18 carbon atoms, hydroxypropyl-piperazinyl-hydroxypropyl, propionyl-piperazinyl-propionyl and hydroxypropyl-benzylamino-hydroxypropyl.

The polymer can be present in amounts of about 0.1 to 5% and preferably 0.2 to 3% by weight in the various cosmetic compositions of the present invention. These compositions include hair-dressing lotions, creams or gels as the main constituent, shampoos, hair-setting compositions, permanent wave composition or hair compositions, compositons, etc. The polymers can also be employed as an adjuvant in the presence of other components such as anionic, cationic, nonionic, amphoteric or zwitterionic surfactants, oxidizing agents, foam stabilizers or synergists, sequestrants, superfatting agents, thickeners, softeners, antiseptics, preservatives, dyes, perfumes, germicides or other anionic, cationic, amphoteric or nonionic polymers.

The polymers can be used in different compositions whose pH varies from 3 to 11, or in the form of inorganic or organic acid salts, or in the form of free base or, alternatively, the quaternary ammonium salt thereof.

The cosmetic compositions for hair according to the present invention can be in the form of an aqueous solution, a dilute alcohol solution, a cream, a paste, a gel, or a powder. They can also contain a conventional aerosol propellant such as dichlorodifluoromethane, monochlorotrifluoromethane, mixtures thereof or other conventional aerosol propellants, and can be packaged in a conventional aerosol bomb under pressure.

The hair shampoo compositions according to the invention are characterized by the fact that they contain, in addition to an anionic, cationic, nonionic, amphoteric and/or zwitterionic surfactant, one or more compounds of formula I and optionally foam stabilizers or synergists, sequestrants, superfatting agents, thickeners, one or more other cosmetic resins, softeners, dyes, perfumes, antiseptics, preservatives and any other adjuvant usually used in cosmetic compositions.

The polymers of formula I also make it possible to prepare hair-setting lotions, hair-setting reinforcers, treatment creams, hair conditioners, anti-dandruff lotions and other similar compositions characterized by the fact that they contain one or more polymers of formula I having a molecular weight, determined by lowering of the vapor tension, between 1,000 and 15,000, or the quaternary ammonium salt or amine oxide of these polymers, possibly mixed with other cosmetic resins.

EXAMPLES OF PREPARATION OF THE POLYMER

EXAMPLE 1

Polycondensation of piperazine and epichlorohydrin.

To a solution of 97 g (0.5 mole) of piperazine hexahydrate in 125 g of water, there are added, drop by drop, over a period of one hour, 46.3 g (0.5 mole) of epichlorohydrin, with stirring, while maintaining the temperature at 20° C. Stirring is continued for 1 hour at 20° C. The reaction mass is then heated at 90°–95° C for 2 hours. Over a period of one hour, 0.5 mole of sodium hydroxide is then added in the form of a 40% (50 g) NaOH solution. A cloud then appears in the solution. The temperature is maintained at the 90°–95° C level for 15 minutes more, and the reaction mixture is then cooled with stirring while adding 182 g of water to bring the concentration to 20% of dry extract (14.5% active material and a 5.5% NaCl).

A limpid and almost colorless solution is thus obtained, having a viscosity of 2.5 poises, measured at 25° C.

On evaporation of a dilute solution of the polymer thus prepared, there is obtained a wrinkled film, opaque because of the presence of the sodium chloride, but hard and not sticky.

EXAMPLE 2

Polycondensation of N,N'bis-(2,3-epoxy propyl) piperazine and piperazine.

A polymer similar to that of Example 1, but free of sodium chloride, is prepared by polycondensation of piperazine and N,N'bis(2,3-epoxy propyl) piperazine in an aqueous medium and in stoichiometric proportions. The N,N' bis-(2,3-epoxy propyl) piperazine can be prepared in the following way:

To 86 g (1 mole) of anhydrous piperazine, dissolved in 540 g of isopropanol, there are added, over a 30 minute period at a temperature of 10°–15° C, 185 g of epichlorohydrin (2 moles). This temperature is maintained at this level while the reaction mixture is stirred for 7 hours.

The resulting dichlorohydrin, derived from piperazine, is filtered and dried. It is a white crystalized product having a melting point of 108°–110° C.

50.7 g (0.18 mole) of the dichlorohydrin thus obtained are dispersed in 100 ml of benzene. The suspension is cooled to 10° C. There are then added by fractions, over a 30 minute period, 15.5 g (0.37 mole) of ground sodium hydroxide. This temperature is maintained for 2½ hours. The sodium chloride precipitate is filtered and rinsed with three times 100 ml of benzene.

After elimination of the benzene, under partial vacuum, there are collected 26 g of white solid corresponding, according to functional analyses, to N,N'bis-(2,3-epoxy propyl) piperazine.

25 g (0.125 mole) of product thus prepared are heated with reflux with 10.8 g (0.125 mole) of anhydrous piperazine in 60 g of isopropanol for 3½ hours.

The cationic polymer is then partially precipitated. The solvent is eliminated under partial vacuum and an almost white powder is thus obtained which is soluble in water and which exhibits a melting point of 190° C. The molecular weight of this polymer, measured in chloroform by the method of lowering the vapor tension, is 2460.

EXAMPLE 3

Quaternization of the piperazine and epichlorohydrin polycondensate.

To 200 g of solution obtained according to Example 1 which contains 0.4 equivalent of base nitrogen, there are added 170 g of absolute ethyl alcohol and then 25.3 g (0.2 mole) of benzyl chloride. The reaction mixture is heated at 80° C for 1½ hours. The ethanol is then eliminated under partial vacuum, while re-adding water, to obtain a 10% solution of dry extract.

EXAMPLE 4

Oxidation of the piperazine and epichlorohydrin polycondensate.

To 100 g of solution obtained according to Example 1 which contains 0.2 equivalent of base nitrogen, there are added, at a temperature of 50° C, 7.2 ml (0.13 mole) of 200 volume hydrogen peroxide. The temperature is maintained at this level for 10 hours.

The polymer solution obtained is perfectly limpid and yields, an evaporation, films comparable to those of Example 1.

EXAMPLE 5

Polycondensation of piperazine, benzylamine and epichlorohydrin.

To a solution of 97 g (0.5 mole) of hexahydrated piperazine, in 384 g of isopropyl alcohol, there are added, drop by drop at 15° C, 92.5 g (1 mole) of epichlorohydrin. The resulting solution is maintained, with stirring, at 15° C for 2 hours. Thereafter it is heated to 70° C, and over a 15 minute period, 54 g (0.5 mole) of benzylamine are added. The resulting mixture is heated with reflux for an hour. There are then added, drop by drop, 160 g of methanol solution of sodium methylate (0.98 mole). Heating is continued for 1 hour.

After cooling, the formed sodium chloride is filtered and the isopropanol is eliminated under partial vacuum. After drying under vacuum and in the presence of phosphoric anhydride, a hard, brittle, colorless solid is obtained, having a softening point of 65° C and a molecular weight, measured in absolute ethanol of 1600.

The compound thus obtained is soluble in water in an acid medium and in a dilute alcohol medium. It yields beautiful, hard and very brilliant films, after evaporation of its dilute alcohol solvent.

EXAMPLE 6

Polycondensation of N,N'-bis(2,3-epoxy propyl) piperazine and cetylamine.

24 g (0.1 mole) of cetylamine and 20 g (0.1 mole) of N,N'bis(2,3-epoxy propyl) piperazine prepared according to Example 2, are heated with reflux in 45 g of isopropanol for 15 hours. The resin obtained is soluble in water in an acid medium, such as hydrochloric acid.

EXAMPLE 7

Quaternization of the product obtained in Example 6.

To 68 g of the above isopropanol solution (0.23 equivalent in base nitrogen) there are added, drop by drop at 30° C, 14.6 (0.11 mole) of dimethyl sulfate. Stirring is continued for 2 hours. The solvent is then eliminated under partial vacuum, with water being added to produce a final aqueous solution that is 10% by weight.

The film obtained by evaporation of the dilute solution is rather hard and not sticky.

EXAMPLE 8

Polycondensation of N,N'bis(2,3-epoxy propyl) piperazine and dodecylamine.

18.5 g (0.1 mole) of dodecylamine and 20 g (0.1 mole) of N,N'bis(2,3-epoxy propyl) piperazine, prepared according to Example 2, are dissolved in 90 g of isopropyl alcohol. After 10 hours of heating at reflux, the solvent is eliminated under partial vacuum. There is thus obtained a soft, colorless, transparent resin, soluble in water in the presence of hydrochloric acid and also in alcohol such as ethanol or isopropanol.

The molecular weight of this resin, measured in absolute ethanol, is 2900.

By evaporation of dilute solutions, soft, slightly sticky films are obtained.

EXAMPLE 9

Quaternization of the N,N'-bis(2,3-epoxy propyl) piperazine and dodecylamine polycondensate.

To 30 g of resin obtained according to Example 7 (0.21 equivalent in base nitrogen), dissolved in 40 g of isopropanol, there are added, drop by drop at 30° C, 13.5 g (0.1 mole) of dimethyl sulfate. Stirring is kept up for 2 hours at the same temperature. Then the solvent is eliminated under partial vacuum, with water being added to obtain the resin in the form of a 10 weight percent solution in water.

On evaporation of the dilute aqueous solutions, films are obtained which are always soft but which are no longer sticky.

EXAMPLE 10

Polycondensation of piperazine and N,N'-bis(-chloroacetyl)ethylene diamine.

To a solution of 10.6 g (0.05 mole) of N,N'-bis chloroacetyl ethylene diamine in 125 g of water, there are added 9.7 g (0.05 mole) of hexahydrated piperazine. The mixture is heated for 3 hours at 100° C. While the heating is continued, the acid formed is neutralized by addition, in several fractions, of 0.1 mole of sodium hydroxide in the form of a 40% (10 g) NaOH solution.

A colloidal solution having good film-forming properties is thus obtained.

EXAMPLE 11

Polycondensation of N,N'-bis(2,3-epoxy propyl) piperazine, oleylamine and piperazine.

To a solution of 20 g (0.1 mole) of N,N'-bis(2,3-epoxy propyl) piperazine in 47 g of isopropanol, there are added 10.7 g (0.04 mole) of oleylamine and 5.16 g (0.06 mole) of anhydrous piperazine. After 4 hours of heating at reflux, the solvent is eliminated under reduced pressure. There is then obtained a white solid having a softening point of around 100° C, the product being insoluble in neutral water, but soluble in ethanol and in water in an acid medium such as HCl.

Films obtained by evaporation of the dilute solution are transparent, not sticky and slightly hard.

EXAMPLE 12

Polycondensation of piperazine and diglycidyl ether.

To 6.63 g (0.077 mole) of anhydrous piperazine in 11 g of isopropanol there are added over a 15 minute period at 30° C, 10 g (0.077 mole) of diglycidyl ether. The mixture is heated at reflux for 4½ hours. Then the solvent is eliminated, at reduced pressure, while water is added to obtain a colloidal solution of 5 weight percent active material, i.e. polymer.

Films obtained by evaporation of the dilute solution are opalescent, hard and not sticky.

The diglycidyl ether is prepared by reacting at 15°–20° C a stoichiometric amount of sodium hydroxide on bis(3-chloro 2-hydroxy propyl) ether. The diglycidyl ether is isolated by distillaton under reduced pressure. The boiling point is 80°–85° C/0.05 mm Hg.

EXAMPLE 13

Polycondensation of piperazine and methylene bisacrylamide.

To 15.4 g (0.1 mole) of methylene bisacrylamide provided in paste form with 18.6 g of water, there are added with agitation at a temperature between 0° and 5° C and under a nitrogen atmosphere 86 g of a 10% aqueous solution of piperazine (0.1 mole). The mixture is left standing for 30 hours at 25° C.

The polymer is precipitated by flowing the aqueous solution into a great excess of acetone.

There is thus obtained a white solid having a softening point of about 205° C and a melting point of 260° C.

By evaporating the dilute aqueous solution, there is obtained very hard transparent and non-sticky films.

EXAMPLE 14

Polycondensation of piperazine and piperazine bisacrylamide.

To a solution of 19.4 g (0.1 mole) of piperazine bisacrylamide in 35 g of water, there are added with agitation at a temperature between 0 and 5° C and under a nitrogen atmosphere, 86 g of a 10% aqueous solution of piperazine (0.1 mole). The mixture is left standing for 30 hours at 25° C.

The polymer is precipitated by flowing the aqueous solution in a great excess of acetone.

There is thus obtained a white solid having a softening point of about 205° C and a melting point greater than 260° C.

By evaporating the dilute aqueous solution, there is obtained very hard, transparent and non-sticky films.

EXAMPLE 15

Polycondensation of 1,3-bis piperazine-2-propanol and methylene bisacrylamide.

Method 1

To 15.4 g (0.1 mole) of methylene bisacrylamide provided in paste form with 23.1 g of water there are added with agitation at a temperature between 0 and 5° C under a nitrogen atmosphere, 152.5 g of a standardized aqueous solution containing 22.8 g (0.1 mole) of 1,3-bis piperazine-2-propanol. The mixture is left standing for 30 hours at 25° C.

The polymer is precipitated in accordance with the procedure outlined in Example 14.

There is thus obtained a white solid exhibiting a softening point of 176° C and a melting point of 200°–210° C.

By evaporating the dilute aqueous solution, there is obtained very hard, transparent and non-sticky films.

The 1,3-bis-piperazine-2-propanol, utilized above, can be prepared as follows:

To 688 g (8 moles) of anhydrous piperazine dissolved in 1500 g of isopropanol, there are added 92.5 g (1 mole) of epichlorohydrin over a period of 1 hour at a temperature of 20° C. The resulting reaction mixture is then heated for a period of 1.5 hours at 80° C throughout said period. There are then added over a period of ½ hour 250 g of sodium methylate. The reaction mixture is then cooled and filtered to remove sodium chloride formed during the reaction. The remaining reaction mixture is then concentrated under a partial vacuum thereby eliminating the greatest part of the excess piperazine. The desired compound is isolated by distillation. It is a white solid having a melting point of 78° C and a boiling point of 147°–152° C/0.07 mm Hg.

Method 2

To a solution of 116.4 g (0.6 mole) of piperazine hexahydrate in 353 g of water, there are added in small portions a total of 46.2 g (0.3 mole) of solid methylene bisacrylamide, with agitation at a temperature between 0 to 5° C and under a nitrogen atmosphere. The resulting reaction mixture is left to stand for 24 hours at 25° C. There are then added, little by little, 27.75 g (0.3 mole) of epichlorohydrin over a period of 1 hour while maintaining the temperature of the reaction mixture at 20° C.

The reaction mixture is stirred again for a period of 1 hour at a temperature of 20° C. Then there are added at this temperature over a 1 hour period, 30 g (0.3 mole) of a 40% NaOH solution.

After an additional 1 hour period of stirring the reaction mixture at 20° C, the reaction mixture is heated for 1 hour at 60° C. There is thus obtained a 20% solution of the polymer exhibiting a very light opalescence and being nearly colorless. By evaporating the dilute aqueous solution there is obtained a very hard, transparent and non-sticky film.

EXAMPLE 16

Polycondensation of 1,3-bis piperazine-2-propanol and piperazine bisacrylamide.

To a solution of 19.4 g (0.1 mole) of piperazine bisacrylamide in 39.1 g of water, there are added with stirring at a temperature between 0° to 5° C and under a nitrogen atmosphere 152.5 g of a standardized aqueous solution containing 22.8 g (0.1 mole) of 1,3-bis piperazine 2-propanol. The resulting reaction mixture is left to stand for 30 hours at 25° C. The polymer is precipitated from the reaction mixture in accordance with the procedure outlined in Example 14 thereby yielding a white solid having a melting point of about 205°–210° C. By evaporating the dilute aqueous solution there is obtained a hard, transparent and non-sticky film.

The following Table summarizes the reactions of Examples 1 – 16.

TABLE

| | | |
|---|---|---|
| Structural Pattern | —A—B—A—B— (I)<br>—A—B—A—B'—A—B'—A—B (II) | |
| Example No. | Reaction | Formula of Repeating Units |
| 1 | Condensation of piperazine and epichlorohydrin | ⟨N⟩N—CH$_2$—CH(OH)—CH$_2$—<br>—A— —B— |
| 2 | Condensation of N,N' bis-(2,3-epoxy propyl)piperazine and piperazine - MW=2460 | —CH$_2$—CH(OH)—CH$_2$—⟨N⟩N—CH$_2$—CH(OH)—CH$_2$—⟨N⟩N—<br>—B— —A— —B— —A— |
| 5 | Condensation of piperazine, benzylamine and epichlorohydrin - MW=1600 | ⟨N⟩N—CH$_2$—CH(OH)—CH$_2$—N(CH$_2$C$_6$H$_5$)—CH$_2$—CH(OH)—CH$_2$—<br>—A— —B— |
| 6 | Condensation of N,N' bis-(2,3-epoxy propyl)piperazine and cetylamine | ⟨N⟩N—CH$_2$—CH(OH)—CH$_2$—N(R)—CH$_2$—CH(OH)—CH$_2$—<br>—A— —B—<br>wherein R = cetyl |
| 8 | Condensation of N,N' bis(2,3-epoxy)propyl)piperazine and dodecylamine | same as above but R = dodecyl |
| 10 | Condensation of piperazine and N,N' bis(chloroacetyl) ethylene diamine | ⟨N⟩N—CH$_2$—CO—NH—CH$_2$—CH$_2$—NH—CO—CH$_2$—<br>—A— —B— |
| 11 | Condensation of N,N' bis(2,3-epoxy propyl) piperazine, oleylamine and piperazine | ⟨N⟩N—CH$_2$—CH(OH)—CH$_2$—N(R)—CH$_2$—CH(OH)—CH$_2$—⟨N⟩N—CH$_2$—CH(OH)—CH$_2$—N—CH$_2$—CH(OH)—CH$_2$—⟨N⟩N—<br>—A— —B— —A— —B'— —A—<br>wherein R = oleyl |
| 12 | Condensation of piperazine and diglycidyl ether | ⟨N⟩N—CH$_2$—CH(OH)—CH$_2$—O—CH$_2$—CH(OH)—CH$_2$—<br>—A— —B— |
| 13 | Condensation of piperazine and methylene bis-acrylamide | ⟨N⟩N—CH$_2$—CH$_2$—CONH—CH$_2$—NH—CO—CH$_2$—CH$_2$—<br>—A— —B— |
| 14 | Condensation of piperazine and piperazine bis-acrylamide | ⟨N⟩N—CH$_2$—CH$_2$—C(=O)—N⟨N⟩N—C(=O)—CH$_2$—CH$_2$—<br>—A— —B— |
| 15 | Condensation of 1,3-bis-piperazine-2-propanol and methylene bisacrylamide | |

TABLE-continued

| | Structural Pattern | —A—B—A—B— (I)<br>—A—B—A—B'—A—B'—A—B (II) |
|---|---|---|
| Example No. | Reaction | Formula of Repeating Units |

$$-\underset{\underset{-A-}{\underbrace{\phantom{XXX}}}}{N{\diagup\!\!\!\!\diagdown}N}-\underset{\underset{B}{\underbrace{\phantom{XXXXXXX}}}}{CH_2-CHOH-CH_2}-\underset{\underset{-A-}{\underbrace{\phantom{XXX}}}}{N{\diagup\!\!\!\!\diagdown}N}-\underset{\underset{B'}{\underbrace{\phantom{XXXXXXXXXXXXXXXXXXX}}}}{CH_2-CH_2-CONH-CH_2-NHCO-CH_2-CH_2}-$$

16     Condensation of 1,3-bis-piperazine-2-propanol and piperazine bisacrylamide $$-\underset{\underset{-A-}{\underbrace{\phantom{XXX}}}}{N{\diagup\!\!\!\!\diagdown}N}-\underset{\underset{B}{\underbrace{\phantom{XXXXXXX}}}}{CH_2-CHOH-CH_2}-\underset{\underset{-A-}{\underbrace{\phantom{XXX}}}}{N{\diagup\!\!\!\!\diagdown}N}-\underset{\underset{B'}{\underbrace{\phantom{XXXXXXXXXXXXXXXXX}}}}{CH_2-CH_2-\overset{O}{\overset{\|}{C}}-N{\diagup\!\!\!\!\diagdown}N-\overset{O}{\overset{\|}{C}}-CH_2-CH_2}-$$

EXAMPLES OF APPLICATION

Example 17
Setting lotion for very dry hair

| | | |
|---|---|---|
| Compound prepared according to Example 1 | 1 | g |
| Propyl para-hydroxybenzoate | 0.4 | g |
| Neolane pink dye, C.I. 18810 | 0.005 | g |
| Perfume | 0.2 | g |
| Water, q.s.p. | 100 | g |

Example 18
Setting reinforcer for damaged hair

| | | |
|---|---|---|
| Compound prepared according to Example 1 | 1 | g |
| Vinyl pyrrolidone/vinyl acetate 60/40 copolymer (M.W. 50,000 to 70,000) | 0.5 | g |
| Trimethyl cetyl ammonium bromide | 0.2 | g |
| Perfurm | 0.1 | g |
| Methyl para-hydroxybenzoate | 0.1 | g |
| Water, q.s.p. | 100 | g |

Example 19
Setting reinforcer for normal hair

| | | |
|---|---|---|
| Compound prepared according to Example 1 | 1 | g |
| Vinyl acetate/crotonic acid copolymer (M.W. 20,000) | 1 | g |
| Trimethyl cetyl ammonium bromide | 0.1 | g |
| Methyl violet dye, C..I. 42535 | 0.002 | g |
| Perfume | 0.1 | g |
| Ethyl alcohol, q.s.p. 50° | | |
| Water, q.s.p. | 100 | g |

Example 20
anionic shampoo

| | | |
|---|---|---|
| Compound prepared according to Example 1 | 1 | g |
| R—(OCH$_2$—CH$_2$)$_2$—OSO$_3$Na wherein R = alkyl C$_{12}$–C$_{14}$ in proportions of 70/30 | 10 | g |
| Diethanolamide of copra fatty acids | 3 | g |
| Water, q.s.p. | 100 | g |
| pH = 7 | | |

Example 21
Anionic shampoo

| | | |
|---|---|---|
| Compound prepared according to Example 1 | 0.75 | g |
| Triethanolamine alkyl slfate wherein alkyl = C$_{12}$/C$_{14}$ 70/30 | 15 | g |
| Monoethanolamide of copra fatty acid | 4 | g |
| Sodium N-lauryl sarcosinate | 3 | g |
| Acetylated lanolin | 3 | g |
| Water, q.s.p. | 100 | g |
| pH = 7.5 | | |

Example 22
Non-ionic shampoo

| | | |
|---|---|---|
| Compound prepared accordng to Example 1 | 2.5 | g |
| $R{-}\left(-OCH_2-\underset{\underset{CH_2OH}{\|}}{CH}-\right)_4-OH$ wherein R = alkyl C$_{12}$H$_{25}$ | 15 | g |
| Alkoxylated anhydrous lanolin sold under the trademark "Lantrol AWS" by Malstrom Chemical Corporation, New Jersey | 1.5 | g |
| Hydroxypropyl methyl cellulose | 0.3 | g |
| Citric acid, q.s.p. pH 6 | | |
| Water, q.s.p. | 100 | g |

-continued
EXAMPLES OF APPLICATION

Example 23
Cationic shampoo
| | | |
|---|---|---|
| Compound prepared according to Example 8 | 1.5 | g |
| Bromide of dodecyl, tetradecyl and hexadecyl trimethylammonium sold under the tradename "Cetavlon" | 5 | g |
| Lauryl alcohol oxyethylenated with 12 moles of ethylene oxide | 12 | g |
| Lauryl diethanolamide | 5 | g |
| Ethyl cellulose | 0.25 | g |
| Lactic acid, q.s.p. pH 4 | | |
| Water, q.s.p. | 100 | g |

Example 24
Amphoteric shampoo
| | | |
|---|---|---|
| Compound prepard according to Example 1 | 1.2 | g |

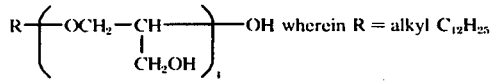

sold under the name Miranol "C2M" by
Miranol CHemical Corporation, Irvington,
| | | |
|---|---|---|
| New Jersey | 20 | g |
| Dimethyl alkylamine oxide prepared from copra fatty acids | 5 | g |
| Lauryl diethanolamide | 2.5 | g |
| Lauryl alcohol, oxyethylenated with 12 moles of ethylene oxide | 8 | g |
| Lactic cid, q.s.p. pH 6 | | |
| Water, q.s.p. | | |

Example 25
Amphoteric shampoo
| | | |
|---|---|---|
| Compound prepared according to Example 1 | 1 | g |
| Sodium salt of N,N(diethylamino propyl)$N^2$-dodecyl asparagin | 5 | g |

$$R\left(OCH_2-CH\underset{CH_2OH}{|}\right)_t OH \text{ wherein } R = \text{alkyl } C_{12}H_{25}$$

| | | |
|---|---|---|
| Lactic acid, q.s.p. pH 5 | | |
| Water, q.s.p. | 100 | g |

Example 26
Anionic shampoo
| | | |
|---|---|---|
| Compound prepared according to Example 9 | 1 | g |
| Sodium alkyl sifate (alkyl = $C_{12}$–$C_{14}$) | 10 | g |
| Sodium N-lauryl sarcsinate | 3 | g |
| Lauryl monoethanolamide | 4 | g |
| Glycol distearate | 3 | g |
| Water, q.s.p. | 100 | g |
| pH = 7 | | |

Example 27
Anionic shampoo
| | | |
|---|---|---|
| Compound prepared according to Example 9 | 0.5 | g |
| $R-O(CH_2CH_2)_2OSO_3Na$ wherein $R = C_{14}H_{29}$ | 10 | g |
| Sodium salt of N,N(diethylamino propyl)-$N^2$-dodecyl sparagin | 3 | g |
| Diethanolamide of copra fatty acids | 3 | g |
| Hydroxypropyl cellulose | 0.2 | g |
| Water, q.s.p. | 100 | G |
| pH = 6.5 | | |

Example 28
Cream for treating dry hair
| | | |
|---|---|---|
| Compound prepared according to Example 1, q.s.p. | 3 | g |
| Cetyl alcohol | 2 | g |
| Stearyl alcohol | 2 | g |
| Cetyl-stearyl alcohol oxyethylenated with 15 moles of ethylene oxide | 4 | g |
| Hydroxyethylcellulose | 2 | g |
| Perfurm | 0.2 | g |
| Water, q.s.p. | 100 | g |

Application of this cream is followed by rinsing of the hair.

Example 29
Conditioner for dry hair
| | | |
|---|---|---|
| Compound prepared according to Example 1, q.s.p. | 0.5 | g |
| Vinyl/pyrrolidone/vinyl acetate copolymer 70/30 (M.W. 40,000) | 0.5 | g |
| Perfume | 0.15 | g |
| Water, q.s.p. | 100 | g |

This conditioner is to be used after shampooing and before setting, without intermediate rinsing.

EXAMPLES OF APPLICATION

Example 30
Anti-dandruff lotion for daily use

| | | |
|---|---|---|
| Compound prepared according to Example 1, q.s.p. | 0.5 | g |
| Lauryl isoquinolinium bromide | 1.3 | g |
| Lactic acid, q.s.p. pH = 5–5.3 | | |
| Ethyl alcohol | 55 | cc |
| Mentol pantothenate | 0.1 | g |
| Perfume | 0.3 | g |
| Water, q.s.p. | 100 | g |

Example 31
Anionic shampoo in the form of a clear solution

| | | |
|---|---|---|
| Ammonium alkylsulfate (alkyl derived from copra) | 3 | g |
| Sodium alkyl ether sulfate wherein the alkyl moiety is derived from copra fatty acids and oxyethylenated with 2 moles of ethylene oxide | 7 | g |
| Compound prepared according to Example 4 | 1 | g |
| Lauryl diethanolamide | 3 | g |
| Mixture of mono- and di-glycerides of fatty acids, sold under the tradename "ARLACEL 186" by Atlas | 0.5 | g |
| Lactic acid, q.s.p. pH 7.5 | | |
| Water, q.s.p. | 100 | g |

Example 32
Anionic shampoo

| | | |
|---|---|---|
| Sodium alkyl ether sulfate wherein the alkyl moiety is derived from copra fatty acids and oxyethylenated with 2 moles of ethylene oxide | 10 | g |
| Copra diethanolamide | 3 | g |
| Compound prepared according to Example 13 | 0.8 | g |
| Sodium monolauryl sulfosuccinate | 2 | g |
| Lactic acid, q.s.p. pH 7.5 | | |
| Water, q.s.p. | 100 | G |

Hair treated with the above composition is easy to comb, exhibits good volume, is shiny and lively.

EXAMPLE 33

Anionic shampoo

The composition of Example 32 is repeated except that the compound prepared according to Example 13 is replaced with an essentially equivalent amount of the compound prepared according to Example 14. Essentially similar effective and advantageous results are achieved with this composition.

EXAMPLE 34

Anionic shampoo

| | | |
|---|---|---|
| Triethanolamine lauryl sulfate | 10 | g |
| Lauryl diethanolamide | 2 | g |
| Compound prepared according to Example 3 | 1 | g |
| Hydroxy propyl methyl cellulose | 0.1 | g |
| Lactic acid, q.s.p. pH 7.2 | | |
| Water, q.s.p. | 100 | g |

This solution imparts to hair a lively and shiny appearance.

Further in Examples 17 – 22, 24, 25 and 28 – 30, the compound prepared in accordance with Example 1 is replaced with the compound prepared in accordance with Examples 15 and 16 in essentially equivalent amounts to provide equally effective hair treating compositions.

In all of the Examples of Application given above, the weight of the polymer is expressed as the active material therein.

EXAMPLE 35

Polycondensation of piperazine, dodecylamine and epichlorohydrin and quaternization of the resulting polycondensate with dimethyl sulfate.

Stage 1 - Polycondensation

To a solution containing 258 g (3 moles) of piperazine, 185 g (1 mole) of dodecylamine and 1000 cc of isopropanol, there are added with agitation at 20° C and over a 2 hour period, 370 g (4 moles) of epichlorohydrin. The reaction mixture is maintained under agitation initially for 2 hours at 20° C and then for 45 minutes at 90° C. At this temperature, over a two hour period, there are added 400 g of a 40% solution of NaOH (4 moles).

The resulting sodium chloride is eliminated by filtration and the isopropanol is eliminated by evaporation under reduced pressure.

There is thus obtained a polymer wherein Z represents B and B', the ratio of A/B/B' = 3/2/1. The formula for units A, B and B' are A: 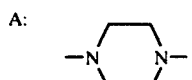

B: 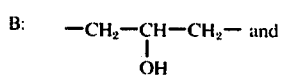

B': 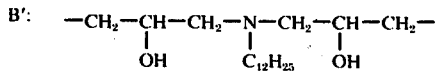

Stage 2 - Quaternization

To 426 g of the above solution, containing 5.92 equivalents of nitrogen, there are added with agitation and at 35° C, 426 g (3.38 moles) of dimethylsulfate. The isopropanol is eliminated in the form of an azeotrope with water and replaced by water in an amount to provide an aqueous solution having 50% active material therein. The resulting solution is clear and very viscous and is comprised essentially of the following units:

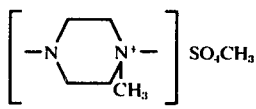

obtained by the quaternization of unit A,

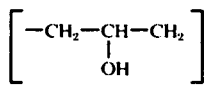

unit B and

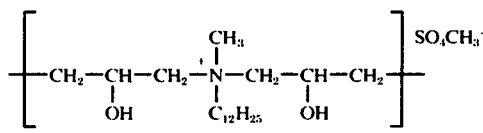

obtained by the quaternization of unit B'.

EXAMPLE 36

Polycondensation of piperazine and isopropylidene bisacrylamide.

To 40.2 (0.22 mole) of isopropylidene bisacrylamide prepared in a known manner, there are added 19 g of piperazine (0.22 mole) dissolved in 236 g of water. The resulting reaction mixture is then heated for three hours with agitation at 45° C. The resulting polymer which is precipitated from the aqueous solution by the addition of a great excess of acetone is isolated by drying, thus yielding a white solid having a melting point of 187°–191° C, a molecular weight equal to 4500 and being soluble in water.

The film obtained by evaporation of a dilute aqueous solution of said polymer is hard, transparent and non-sticky.

This polymer carries the following A and B units:

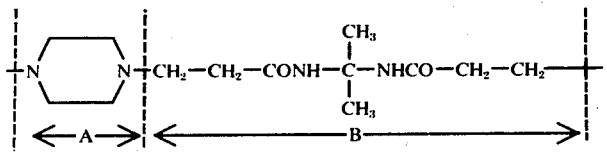

EXAMPLE 37

50% quaternization using dimethyl sulfate of the polymer obtained by the polycondensation of piperazine and epichlorohydrin.

To 200 g of a 10% aqueous solution of the polymer prepared in Example 1 and containing 0.284 atom of nitrogen, there are added at 30° C and with agitation, 18 g (0.142 mole) of dimethyl sulfate. Agitation is maintained for 4 hours at this temperature. A 15% solution of the polymer as the active material is produced by the addition thereto of 35 g of water.

On evaporation of an aqueous solution containing said polymer, a hard, translucent and slightly sticky film is obtained.

EXAMPLE 38

Polycondensation of N,N'-bis(2,3-epoxypropyl) piperazine and octylamine and 50% quaternization with dimethyl sulfate.

Stage 1 - Polycondensation

To 15.5 g (0.12 mole) of octylamine dissolved in 78.5 g of isopropanol, there are added 23.8 g (0.12 mole) of N,N'-bis(2,3-epoxypropyl) piperazine, prepared in accordance with Example 2. The resulting reaction mixture is then heated with agitation for 10 hours at reflux.

Stage 2 - Quaternization

To 82 g of the above solution containing 0.25 atom of nitrogen, there are added 15.75 g (0.125 mole) of dimethyl sulfate while maintaining the temperature at 30° C. After elimination of the solvent by evaporation under reduced pressure, a white solid which is very hygroscopic and is soluble in water and in ethanol is obtained. On evaporation of an aqueous solution containing said polymer, a transparent film sufficiently hard and only slightly sticky is obtained.

The non-quaternized polymer has the following A and B units:

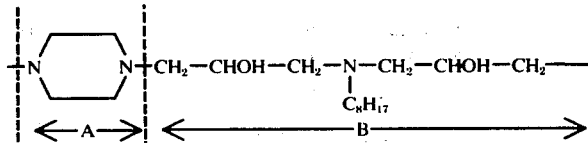

The quaternized polymer has essentially the following units:

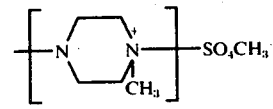

obtained by the quaternization of unit A and

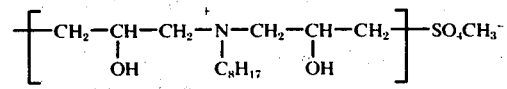

obtained by the quaternization of unit B.

EXAMPLE 39

Polycondensation of bis-(chloroacetyl)piperazine and piperazine.

A suspension of 239 g (1 mole) of bis-(chloroacetyl) piperazine, prepared in a known manner, and 194 g (1 mole) of piperazine hexahydrate in 650 g of water is heated with agitation for ½ at 90° C.

At this same temperature, there are added to the resulting clear solution with agitation, 200 g (2 moles) of a 40% solution of NaOH.

The resulting polymer is isolated by filtration in the presence of acetone and washed first with water and then with acetone.

There is thus obtained a white solid, soluble in water in the presence of an organic or mineral acid. The viscosity of a 10% solution of this polymer in a 90:10 acetone-water mixture measured at 25° C is equal to 0.28 poise.

On evaporation of an aqueous acid solution of the polymer, there is obtained a hard and non-sticky film.

Units A and B of this polymer are as follows:

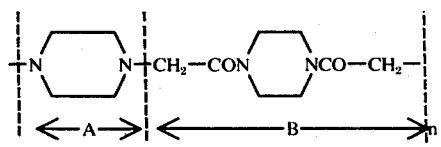

EXAMPLE 40

50% quaternization by dimethyl sulfate of the polymer of Example 39.

To a dispersion in 150 g of water, of 50.40 g of the polymer prepared in accordance with Example 39 and containing 0.4 atom of nitrogen there are added over a period of 1 hour, with agitation and at 30° C, 25.2 g (0.2 mole) of dimethyl sulfate. At the end of the addition, the polymer passes entirely into solution which is then maintained with agitation at 30° C for another hour. On evaporation of an aqueous solution containing the resulting quaternized polymer there is obtained a transparent, hard and non-sticky film.

The quaternized polymer is made up of essentially the following units:

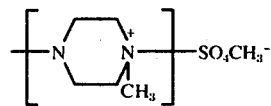

obtained by the quaternization of unit A and

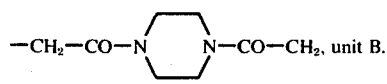

EXAMPLE 41

Polycondensation of piperazine, dodecylamine and N,N'-bis(2,3-epoxypropyl)piperazine and quaternization with methyl methane sulfonate.

Stage 1

To a solution containing 370 g (2 moles) of dodecylamine and 172 g (2 moles) of piperazine in 3500 cc of isopropanol there are added 792 g (4 moles) of N,N'-bis(2,3-epoxypropyl)piperazine. The resulting mixture is then heated with agitation for 6 hours at reflux.

Stage 2

To 139 g of the above solution containing 0.478 equivalent of nitrogen, there are added with agitation and over a period of ½ hour, 30 g (0.273 mole) of methyl methane sulfonate of the formula $CH_3$—$SO_3CH_3$. The resulting mixture is then heated for 3 hours at 50° C. The resulting polymer which is precipitated from the isopropanolic solution by the addition thereto of a great excess of acetone is isolated by drying, thus yielding a white solid which is perfectly soluble in water.

The non-quaternized polymer is made up of the following A, B and B' units:

A: 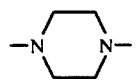

B: 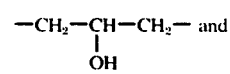  and

B': 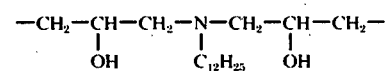

The quaternized polymer is made up of essentially the following units:

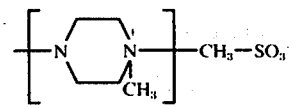

obtained by the quaternization of unit A,

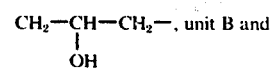, unit B and

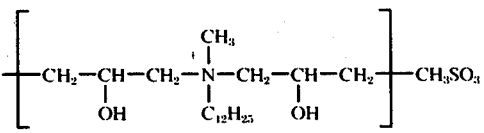

obtained by the quaternization of unit B'.

EXAMPLE 42

Polycondensation of N,N'-bis(2,3-epoxypropyl) piperazine and stearylamine and quaternization of the resulting polycondensate with dimethyl sulfate.

Stage 1 - Polycondensation

To 27 g (0.1 mole) of stearylamine dissolved in 100 g of isopropanol there are added 19.8 g (0.1 mole) of N,N'-bis(2,3-epoxypropyl)piperazine prepared in accordance with the first step set forth in Example 2. The resulting reaction mixture is then heated with agitation for 10 hours at reflux.

Stage 2 - Quaternization

To the above solution containing 0.3 equivalent of nitrogen, there are added 25.2 g (0.2 mole) of dimethyl sulfate while maintaining the temperature at 40° C. The isopropanol is eliminated by evaporation under reduced pressure and replaced partially by water, thus yielding a white solid containing 87% active material.

On evaporation of an aqueous solution containing said polymer, there is obtained a transparent film, slightly hard but not sticky.

The non-quaternized polymer is made up of the following A an B units:

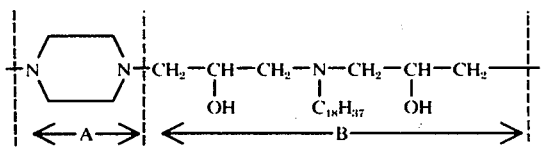

The quaternized polymer is made up essentially of the following units:

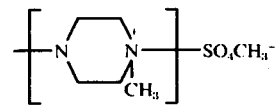

obtained by the quaternization of unit A, and

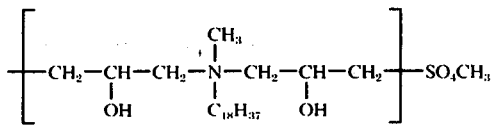

obtained by the quaternization of unit B.

| Example 43 | | |
|---|---|---|
| Anionic Shampoo: | | |
| Compound of Example 36 | 2 | g |
| Triethanolamine lauryl sulfate | 12 | g |
| Diethanolamides of the fatty acids of copra | 3 | g |
| Water, q.s.p. | 100 | g |
| pH = 7.5 | | |
| Example 44 | | |
| Nonionic shampoo: | | |
| $C_{12}H_{25}-O-(C_2H_3O(CH_2OH)_{11}H$ | 8 | g |
| Lauryl alcohol oxyethylenated with 12 moles of ethylene oxide | 6 | g |
| Lauryl diethanolamide | 3 | g |
| Compound of Example 36 | 2 | g |
| Lactic acid, q.s.p. pH 5 | | |
| Water, q.s.p. | 100 | g |
| Example 45 | | |
| Nonionic shampoo: | | |
| $C_{12}H_{25}$ $O-(C_2H_3O(CH_2OH)_{11}H$ | 7 | g |
| Lauryl alcohol oxyethylenated with 12 moles of ethylene oxide | 7 | g |
| Lauryl diethanolamide | 3 | g |
| Compound of Example 39 | 1.1 | g |
| Triethanolamine, q.s.p. pH 7.5 | | |
| Water, q.s.p. | 100 | g |

This clear formulation when applied to the hair provides an abundant foam. After rinsing, the hair untangles easily. At the time of styling, the hair is lively, full and shiny.

EXAMPLE 46

| Nonionic shampoo: | | |
|---|---|---|
| $C_{12}H_{25}O-(C_2H_3O(CH_2OH)_{11}H$ | 15 | g |
| Compound of Example 39 | 2 | g |
| 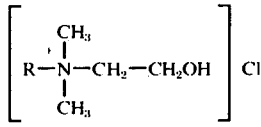 | | |
| wherein R is a radical derived from fatty acids of tallow | 0.5 | g |
| Lactic acid, q.s.p. pH 3 | | |
| Water, q.s.p. | 100 | g |

This clear formulation when applied to the hair provides an abundant foam which is easily removed. Wet hair thus treated untangles very easily. After rinsing the hair is soft, shiny and light.

In accordance with a second embodiment of the invention, the low molecular weight film forming cationic polymer is of the type $$- A - Z -$$ (I bis)

wherein unit A represents

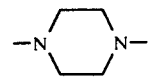

and unit Z represents unit $B'_1$ or both $B_1$ and $B'_1$ with the proviso that at least one unit $B'_1$ is present. $B_1$ represents straight or branched chain alkylene having up to 7 carbon atoms in the principal chain, substituted by a hydroxy group. Preferably the unit $B_1$ is 2-hydroxy propane 1,3-diyl. $B'_1$ represents a bivalent straight or branched chain alkylene having up to 7 carbon atoms in the principal chain, either unsubstituted or substituted by one or more hydroxy radicals and interrupted by one or more nitrogen atoms, the nitrogen atom being substituted by alkyl containing 1–4 and preferably 4 carbon atoms, and optionally being interrupted by an oxygen atom but necessarily carrying one or more hydroxy and/or carboxyl groups. These polymers of the second embodiment of this invention exhibit, as those of the first embodiment, desirable properties for treating and conditioning the hair. In addition to the advantages of hair conditioning such as the improvement in untangling wet hair, brilliance, softness and ease of styling the hair, the polymers of the second embodiment of the present invention exhibit improved compatibility vis-a-vis surface active agents conventionally used in compositions for the treatment of hair and particularly vis-a-vis anionic surface active agents.

The cosmetic composition for the hair can also include (1) the product of oxidation of a polymer of formula I bis obtained preferably by reaction with $H_2O_2$ or with a peracid or (2) a quaternary ammonium salt of the polymer of formula I bis. The said polymer has a molecular weight of about 1,000 to 15,000.

It has also been found that cosmetic compositions for the hair conditioning a polymer of the formula $$-A-Z-A-Z-A-Z- \quad (1)$$

or of the type $$-A-Z- \quad (\text{I bis})$$

can be improved by using the quaternary ammonium salts of said polymers obtained by quaternization of the basic groups thereof with chloroacetic acid or a chloroacetate salt for example sodium chloroacetate. This improvement resides principally in an enhanced compatibility of the thus quaternized polymers vis-a-vis anionic surface active agents conventionally employed in said compositions.

Thus, the second embodiment of this invention relates to cosmetic compositions for the treatment and conditioning of hair, containing a low molecular weight cationic polymer of the type $$-A-Z- \quad (\text{I bis})$$

wherein A and Z have the meaning given above, the said cationic polymer being essentially characterized by the fact that it contains at least one unit being $B'_1$ wherein $B'_1$ represents a bivalent straight or branched chain alkylene having up to 7 carbon atoms in the principal chain, substituted or not by one or more hydroxy radicals and interrupted by one or more nitrogen atoms, the nitrogen atom being substituted by alkyl having from 1 to 4 and preferably 4 carbon atoms and being optionally interrupted by an oxygen atom and necessarily having one more hydroxy and/or carboxyl functions.

The present invention also relates to cosmetic compositions containing compounds resulting from the oxidation or quaternization of the polymers of formula I bis.

The present invention further relates to a film forming cationic polymer of low molecular weight of the formula $$-A-Z- \quad (\text{I bis})$$

where unit A represents

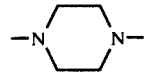

and unit Z represents $B'_1$ or both $B_1$ and $B'_1$ with the proviso that at least one unit $B'_1$ is present. $B_1$ represents a bivalent straight or branched chain alkylene having up to 7 carbon atoms in the principal chain, substituted by a hydroxy group. Preferably the unit $B_1$ is 2-hydroxy propane 1,3-diyl. $B'_1$ represents a bivalent straight or branched chain alkylene having up to 7 carbon atoms in the principal chain, either unsubstituted or substituted by one or more hydroxy radicals and interrupted by one or more nitrogen atoms, the nitrogen atom being substituted by alkyl containing from 1-4 and preferably 4 carbon atoms and optionally interrupted by an oxygen atom but necessarily carrying one or more hydroxy and/or carboxyl functions, as well as the oxidation and quaternization derivatives of these polymers.

The following preferred polymers of the second embodiment of the present invention are particularly polymers of the formula $$-A-Z- \quad (\text{I bis})$$

wherein unit A represents

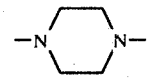

and unit Z represents $B_1$ and $B'_1$ wherein $B_1$ represents hydroxyalkylene such as 2-hydroxy propane 1,3-diyl; $B'_1$ represents polyhydroxy alkylene and preferably dihydroxy alkylene, having preferably 6 carbon atoms, interrupted by a nitrogen atom and substituted by a member selected from the group consisting of carboxymethyl, 2-β-hydroxyethoxy ethyl, 1,3-dihydroxy-2-methyl-propyl-2 and 1-hydroxy-2-methyl-propyl-2.

The present invention also relates to a process for preparing said polymers and their quaternary ammonium derivatives.

The following cationic polymers of the second embodiment of the present application can be prepared by direct or indirect polycondensation.

Direct polycondensation comprises reacting piperazine and a hydroxylated amine such as diglycolamine or 2-amino-2-methyl propane-1,3-diol or an amino acid such as glycocol with an epihalohydrin such as epichlorohydrin or epibromohydrin, in an aqueous medium, to which has been added NaOH as the acceptor of the liberated hydro acid, then heating to a temperature between 80° and 90° C.

Indirect polycondensation comprises first preparing an intermediate derivative X, resulting from the reaction of epihalohydrin with either piperazine, or hydroxylated amine and/or amino acid. This intermediate derivative X is then reacted with a second amine. There is then added, optionally, epihalohydrin and a base such as sodium hydroxide. The resulting mixture is subsequently heated to a temperature between 80 and 90° C.

The epihalohydrin and the piperazine-hydroxylated amine and/or amino acid mixture are preferably present in equimolar proportions. As for the piperazine-hydroxylated amine and/or amino acid mixture, the said mixture includes a molar proportion ranging between 90 and 50% for the piperazine and 10-50% for the hydroxylated amine and/or amino acid.

The resulting polymers of the second embodiment of the invention can, in the manner indicated with respect to the polymers of the first embodiment, be oxidized with $H_2O_2$ or with a peracid, or be quaternized with known quaternization agents such as a bromide, chloride, iodide, sulfate, mesylate, or lower alkyl tosylate, preferably methyl or ethyl tosylate, benzyl chloride or benzyl bromide.

As indicated above, a further quaternization type reaction, which surprisingly has proved to be particularly advantageous insofar as imparting enhanced compatability characteristics to polymers of this invention vis-a-vis anionic surface active agents, can be effected. This particular quaternization reaction is referred to as the "betainization" of compounds of polymers of formulas I and I bis and comprises quaternizing from 0–66 percent of the quaternizable basic groups with a chloroacetate preferably sodium chloroacetate or chloroacetic acid. The yield of the reaction is generally between 60 – 100 percent.

The amount of "betainization" can be defined as the ratio between the number of equivalents of nitrogen quaternized and the total number of quaternizable nitrogens multiplied by 100.

The yield of this particular type of quaternization reaction can be defined by the ratio between the number of equivalents of nitrogen actually quaternized and the number of equivalents of the quaternization agent employed, multiplied by 100.

It has been noted that only one of the two atoms of tertiary nitrogen of unit A is easily quaternized. By the present "betainization" reaction, there is thus produced a polymer of the formula $-A'-Z'-$ (II) wherein unit A' is a mixture of the groups

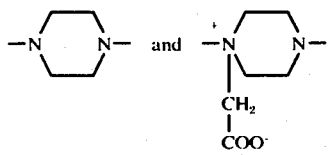

and Z' represents either $B_1$ or the units obtained by betainization of units B, B' or $B'_1$ when these units carry one or more basic nitrogen atoms and thus can take the form

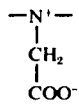

Thus, the present invention also relates to a polymer of the formula $$-A'-Z'- \quad (II)$$

where unit A' represents a mixture of the radicals

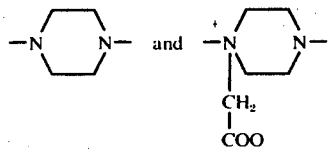

and unit Z' represents:

(1) either B or else B' or the units obtained by betainization of B or B' when they carry one or more basic nitrogen atoms; B and B' each independently represent a bivalent straight or branched chain alkylene carrying up to 7 carbon atoms in the principal chain, unsubstituted or substituted by one or more hydroxyl groups and capable of carrying additional atoms of oxygen, nitrogen, sulfur, 1–3 aromatic or heterocylic rings, the oxygen, nitrogen and sulfur atoms being present in the form of an ether, thioether, sulfoxide, sulfone, sulfonium, amine, alkylamine, alkenylamine, benzylamine, amine oxide, amide, imide, alcohol, ester and/or urethane groups; or (2) either Z' represents $B_1$ or else $B'_1$ and the units obtained by betainization of $B'_1$ with the proviso that at least one unit $B'_1$ or a unit derived from $B'_1$ is present;

$B_1$ represents a bivalent straight or branched chain alkylene having up to 7 carbon atoms in the principal chain, substituted by a hydroxyl group and preferably a 2-hydroxy propane 1,3-diyl group; $B'_1$ is a bivalent radical straight or branched chain alkylene having up to 7 carbon atoms in the principal chain, either unsubstituted or substituted by one or more hydroxy radicals and interrupted by one or more nitrogen atoms, the nitrogen atom being substituted by alkyl containing 1 to 4 and preferably 4 carbon atoms and optionally being interrupted by an oxygen atom but necessarily carrying one or more hydroxy and/or carboxyl functions.

The present case has also for an object a cosmetic composition the for hair including a polymer of the formula $$-A'-Z'- \quad (II)$$

wherein A' and Z' have the meanings given above.

The polymers of the present invention prepared in accordance with any of the processes described above are not only film forming and have a relatively low molecular weight, i.e. lower than 15,000, but they are also soluble in water or in a hydroalcoholic medium.

These polymers are particularly effective for hair which has become sensitized due to such treatments as bleaching, permanent waving or dyeing. However, these polymers can also advantageously be used for normal hair.

The polymers of the present invention are employed in an amount of 0.1–5 percent, preferably 0.2 to 3 percent of the total weight of the cosmetic composition which can take any one of a variety of forms. When the form of the cosmetic composition selected is a lotion, cream, or styling gel, the polymer of the present invention can be included therein as the principal component. When the form of the cosmetic composition chosen is a shampoo, wave setting lotion, permanent wave formulation, dye composition and the like, the polymer can be present as the adjuvant therein together with other components such as anionic, cationic, nonionic, amphoteric or zwitterionic surface active agents, an oxidizing agent, a synergestic agent, a foam stabilizer, a sequesterant, a superfatting agent, a thickener, a softener, an antiseptic agent, a preservative, a dye, a perfume, or a germicide. Further, the polymer of the present invention can also be employed in admixture with other anionic, cationic, amphoteric or nonionic polymers.

The polymers of the present invention can also be present in the various cosmetic compositions described above in the form of a salt of a mineral or organic acid, or in the form of free bases or in the form of a quaternary thereof, depending for instance on the pH of the particular cosmetic selected, the said pH ranging generally between 3 and 11.

The cosmetic compositions for the hair in accordance with the present invention can also be in the form of an aqueous, hydroalcoholic or alcoholic solution, a cream, a paste, a gel or a powder. Additionally, the said cosmetic composition can also include a propellant and be packaged in an aerosol container.

The shampoo compositions for the hair in accordance with the present invention comprise in addition to an anionic, cationic, nonionic, amphoteric or zwitterionic surface active agent, one or more polymers of formula I bis and/or II, as well as, optionally, such components as synergistic foam stabilizers, sequesterants, superfatting agents, thickeners, or one or more cosmetic resins, softeners, dyes, perfumes, bactericides, preservatives, and any other adjuvant conventionally employed in such cosmetic compositions.

The polymers in accordance with the present invention also are advantageously employed in the preparation of hair setting lotions, treating creams, hair conditioners, anti-dandruff lotions and other similar compositions, characterized by the fact that they include one or more polymers of the present invention having a molecular weight, determined by lowering of the vapor pressure, ranging between 500 and 15,000.

The following non-limiting examples illustrate the invention. Unless otherwise indicated, all parts and percentages are by weight.

EXAMPLE 47

1st stage - Preparation of intermediate derivative: N,N-bis[β-hydroxy, γ-chloro-propyl] diglycolamine of the formula Cl—CH₂—CHOH—CH₂—N—CH₂—CHOH—CH₂—Cl
                    |
                    CH₂
                    |
                    CH₂—O—CH₂—CH₂OH hereafter referred to as intermediate X.

There are added dropwise to a solution of 420 g (4 moles) of diglycolamine in 2700 g of water, with agitation, 740 g (8 moles) of epichlorohydrin over a one hour period at 10°–15° C.

After 4 hours of agitating the resulting reaction mixture at 20° C, the epoxide functions have practically disappeared, yielding a clear, very lightly tinted green solution, having 30% dry extract.

2nd stage - Preparation of a polymer of the type — A — Z — where A represents

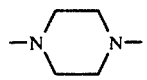

and Z represents $B_1$ or $B'_1$ wherein $B_1$ represents —CH₂—CHOH—CH₂— and $B'_1$ represents

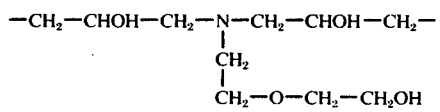

and in which the ratio of units $A/B'_1/B_1$ are 4/1/3, the molar proportions of piperazine/diglycolamine/epichlorohydrin being 4/1/5.

To 775 g (4 moles) of piperazine hexahydrate, there are added, while maintaining the temperature at 20° C, 965 g (1 mole) of a solution of intermediate derivative X prepared above. To the resulting mixture there are added 277 g (3 moles) of epichlorohydrin at a temperature of 20° C. Then, over a period of 1 hour, 500 g (5 moles) of a 40% NaOH solution are added thereto and the resulting mixture is heated to a temperature of 80°–90° C, which temperature is maintained for 1 hour.

On dilution of the reaction mass with 1130 g of water, a 20% solution of active material, i.e. the desired polymer is obtained.

EXAMPLE 48

Direct preparation of a polymer of the type — A — Z — in which the units A and Z have the same meaning as in Example 47 but where the distribution of the piperazine nd diglycolamine is statistical.

The proportion of units $A/B'_1/B_1$ is 4/1/3 is above.

The same relative molar amounts of piperazine, diglycolamine and epichlorohydrin as in Example 47 are employed, i.e. 4/1/5.

To 161 g (0.83 mole) of piperazine hexahydrate and 21 g (0.2 mole) of diglycolamine, dispersed in 140 ml of water, there are added over a one hour period and at 20° C, 92.5 g (1 mole) of epichlorohydrin. One hour after the said addition, there are added dropwise, again at 20° C, 100 g of a 40% (1 mole) solution of NaOH. The resulting mixture is then heated to a temperature of 80°–90° C, which temperature is maintained for 1 hour.

The reaction medium is then diluted with 227 ml of water, this yielding a solution having 20% of the desired polymer. This solution is colorless and has a viscosity of 0.7 poise measured at 25° C.

EXAMPLE 49

Preparation of a polymer of the type — A — Z — wherein
A represents

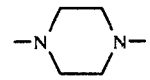

and Z represents $B'_1$ wherein $B'_1$ represents

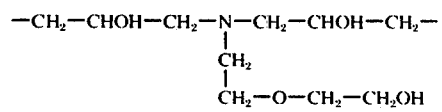

The proportion of units $A/B'_1$ is 1/1.

The molar proportions of piperazine/diglycolamine/epichlorohydrin are 1/1/2.

To a solution of 1 mole (194 g) of piperazine hexahydrate in 742 g of water, there is added, dropwise, over a 1 hour period, at 20° C, with agitation and under a nitrogen atmosphere, 1 mole of intermediate X prepared in Example 47, in the form of a 30% solution (970 g).

At the end of the addition, the reaction mass is maintained under agitation at 20° C, for 1 hour.

There are then added, at the same temperature and over a 1 hour period, 167.5 g of 48% NaOH (2 moles).

Agitation is again maintained for 1 hour at this temperature at which time the mixture is then heated for 2 hours at 80°–90° C.

On addition of 1026.5 g of water, a clear and practically colorless solution containing 10% polymer as the active material is obtained.

EXAMPLE 50

1st stage - Preparation of a prepolymer P to which has been assigned the following formula:

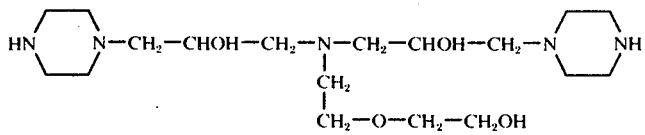

To a solution of 776 g (4 moles) of piperazine hexahydrate in 500 g of water, there are added by proceeding as in Example 49, 2 moles of the intermediate derivative X of Example 47 in the form of a 30% solution (1935 g).

At the end of the addition, the reaction mass is maintained under agitation at 20° C for 1 hour.

At the same temperature and over a 1 hour period, there are added 4 moles of sodium hydroxide in the form of a 48% solution (335 g). Agitation is maintained again for 1 hour at this temperature at which point the mixture is heated for 2 hours at 80°–90° C, thereby yielding a clear solution of prepolymer P defined above.

2nd stage - Preparation of a polymer of the type — A — Z— wherein A represents

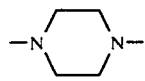

and Z represents $B_1$ and $B'_1$ wherein $B_1$ represents —$CH_2$—CHOH—$CH_2$— and $B'_1$ represents

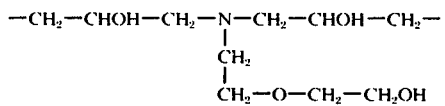

The proportion of units $A/B'_1/B_1$ are 2/1/1.

The molar proportions of piperazine/diglycolamine/epichlorohydrin are 2/1/3.

To a portion of the prepolymer P solution prepared above (1835 g - corresponding to 2 equivalents of secondary amines) there are added, dropwise and with agitation, 92.5 g of epichlorohydrin (1 mole).

At the end of the addition, the reaction mass is maintained under agitation at 20° C for 1 hour, at which point there are added, at the same temperature and over a 1 hour period, 83 g (1 mole) of a 48% NaOH solution. Agitation of the reaction mixture is maintained again for 1 hour at this temperature at which point the reaction mixture is heated for 1 hour at 80°–90° C.

On addition of 2625 g of water thereto, a clear and practically colorless solution containing 10% polymer as the active material is obtained.

EXAMPLE 51

Preparation of a polymer of the type — A — Z — wherein A represents

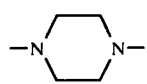

and Z represents $B_1$ and $B'_1$ wherein $B'_1$ represents

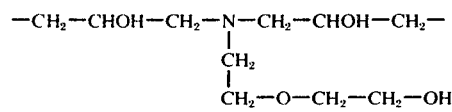

and $B_1$ represents —$CH_2$—CHOH—$CH_2$—.

The proportions of units $A/B'_1/B_1$ are 4/1/3.

The relative molar proportions of piperazine/diglycolamine/epihalohydrin are 4/1/5.

To 394.5 g of prepolymer solution P described above and containing 0.43 equivalent of secondary amine, there are added, with agitation, 51 g of 1,3-bispiperazinyl propane-2-ol having the formula

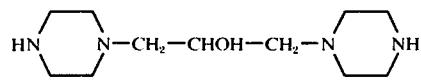

and containing 0.43 equivalent of secondary amine, i.e. corresponding to 0.215 mole. The 1,3-bis piperazino-2-propane-2-ol can be prepared following the method described in Example 15 above.

To this solution there are added over a 1 hour period, and at 20° C, 39.7 g (0.43 mole) of epichlorohydrin. The mixture is agitated for 1 hour at this temperature at which point there are added at 20° C and over a 1 hour period, 35.8 g (0.43 mole) of a 48% NaOH solution.

After 1 hour of agitation at the same temperature, the reaction mass is heated for 1 hour at 80°–90° C.

On addition of 1099 g of water, a clear solution containing 10% polymer as active material is obtained.

EXAMPLE 52

Preparation of a polymer of the type — A — Z — wherein A represents

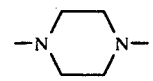

and Z represents $B_1$ and $B'_1$ wherein $B'_1$ represents

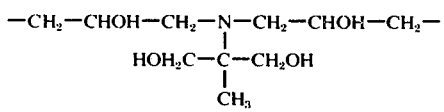

and $B_1$ represents —$CH_2$—CHOH—$CH_2$—.

The proportion of units $A/B'_1/B_1$ is 1/0.42/0.56, the units $B_1$ and $B'_1$ being statistically distributed.

This polymer is prepared in accordance with the direct process of Example 48 above starting with piperazine (1.07 mole), 2-amino-2-methyl propane-1,3-diol (0.45 mole) and epichlorohydrin (1.5 mole).

209 g of piperazine hexahydrate (1.07 mole) and 47.2 g of 2-amino-2-methyl propane 1,3-diol are mixed in 250 ml of water. To the resulting mixture there are added over the space of 1 hour at 20° C, 139 g (1.5 moles) of epichlorohydrin. 150 g of a 40% solution of NaOH (1.5 moles) are then added and the mixture is heated to 80°-90° C, which temperature is maintained for 1 hour.

At the end of the reaction, the reaction mixture is diluted with 760 ml of water, thereby yielding a clear solution having 20% dry extract.

EXAMPLE 53

Preparation of a polymer of the type — A — Z — in which A represents

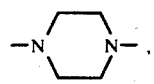

Z represents $B_1$ and $B'_1$ wherein $B'_1$ represents

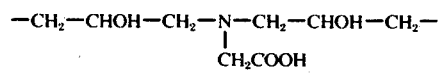

and $B_1$ represents —$CH_2$—CHOH—$CH_2$—.

The proportion of units $A/B'_1/B_1$ is 1.2/0.8/0.4, the units $B_1$ and $B'_1$ being statistically distributed.

The relative molar proportions of piperazine/-glycocol/epichlorohydrin are 1.2/0.8/2.

60 g (0.8 mole) of glycocol having the formula $H_2N$—$CH_2$—COOH and dispersed in 218 g of water are neutralized with 80 g of a 40% solution of NaOH (0.8 mole).

To the above solution, there are added 233 g (1.2 mole) of piperazine hexahydrate. Then, with agitation and over a 1 hour period at 15°-20° C, 185 g (2 moles) of epichlorohydrin are added thereto.

After 1 hour of agitation of this temperature, there are added, at the same temperature, 200 g (2 moles) of a 40% solution of NaOH.

Agitation is again continued initially for 1 hour at 20° C and then for 1 hour at 80° C. The resulting solution is cooled and provides on addition of 124 g of water a 25% solution of the polymer as the active material, the said solution being clear and tinted very lightly yellow. On evaporation of a dilute solution of said polymer, a hard and slightly sticky film is obtained.

EXAMPLE 54

Preparation of a betainized polymer of the type — A' — Z' — wherein A' represents a mixture of the following radicals:

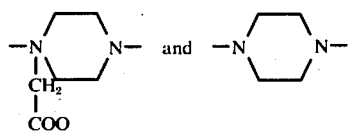

and Z' represents B wherein B represents —$CH_2$—CHOH—$CH_2$—.

To 500 g of an aqueous solution of a polymer of the type — A — Z — wherein A represents

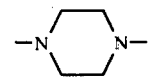

and Z is B wherein B represents —$CH_2$—CHOH—$CH_2$—, said solution containing 14.2% of the polymer as the active material, said polymer being obtained by the condensation in an aqueous solution of 100 g of piperazine hexahydrate (0.51 mole), 47.7 g of epichlorohydrin (0.51 mole) and 20.2 g of sodium hydroxide (0.51 mole), said polymer containing 1 equivalent of quaternizable nitrogen and having a viscosity at 20° C of 320 centipoises, there are added 58.25 g (0.51 mole) of sodium monochloracetate. The resulting mixture is then heated at 90° C for a period of 5 hours. After cooling, the analysis effected on the solution shows a quaternization yield of 83.4% with the amount of betainization being 41.7%. The viscosity of the solution after quaternization is 130 centipoises at 25° C.

The amount of betainization of 41.7% indicates that 83.4% of units A' represent

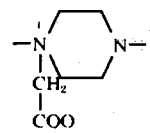

EXAMPLE 55

To 812 g of the aqueous solution of cationic polymer having 14.2% active material described above and containing 1.6 equivalents of quaternizable nitrogen, there are added 46.7 g (0.4 mole) of sodium monochloracetate. The resulting mixture is heated at 90° C for 5 hours. The quaternization yield is 85%. The amount of betainization is 21%.

In this betainized polymer, 42% of the A' units represent

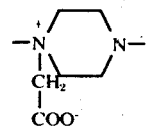

EXAMPLE 56

Preparation of a betainized polymer of the type — A' — Z' — wherein A' represents a mixture of the following radicals:

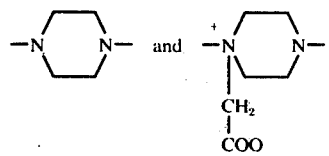

and Z' represent $B_1$, i.e. —$CH_2$—CHOH-$CH_2$—; and the units obtained by betainization of $B'_1$ units, i.e. a mixture of the following radicals:

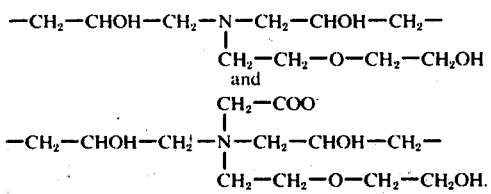

A polymer is obtained by solution condensation of 483 g (2.49 moles) of piperazine hexahydrate, 63 g (0.6 mole) of diglycolamine, 277.5 g (3 moles) of epichlorohydrin and 120 g (3 moles) of NaOH. The solution has a viscosity of 75 cps at 25° C.

This starting polymer is of the type — A — Z —, where A represents

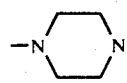

and Z represents $B_1$ and $B'_1$ wherein $B'_1$ represents

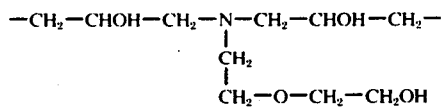

and $B_1$ represents —$CH_2$—CHOH—$CH_2$—.

The proportion of units $A/B'_1/B_1$ is 2.4/0.6/1.8.

To 1005 g of a 20% solution of said polymer containing 2.5 equivalents of total nitrogens, there are added 157.4 g (1.34 moles) of sodium monochloracetate to betainize the said polymer. The resulting mixture is heated at 95° C for 5 hours.

The quaternization yield is 70–71% and the viscosity of the resulting compound is 67 cps at 25° C. The amount of betainization is 37.5% i.e. that 37.5% of the basic nitrogen atoms are in the form of

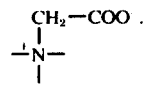

EXAMPLE 57

To 1005 g of a 20% solution of cationic polymer used in Example 56 containing 2.5 equivalents of total nitrogens, there are added 78.8 g (0.67 mole) of sodium monochloracetate. The resulting mixture is heated at 85°–100° C for 5-6 hours. The quaternization yield is 71% and the viscosity after the reaction at 25° C is 60 cps. The amount of betainization is 19%.

The betainized polymer is of the same type as that prepared in Example 56 and differs from it by the fact that 19% of the basic nitrogen atoms are of the form

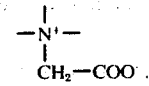

EXAMPLE 58

Quaternization by the use of dimethyl sulfate of the compound of Example 48 wherein A represents

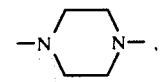

and Z represents $B_1$ and $B'_1$ wherein $B_1$ represents —$CH_2$—CHOH—$CH_2$— and $B'_1$ represents

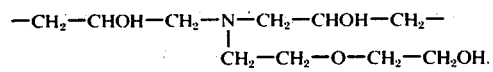

The quaternized polymer is essentially constituted by the following two units in the proportion of 80/20:

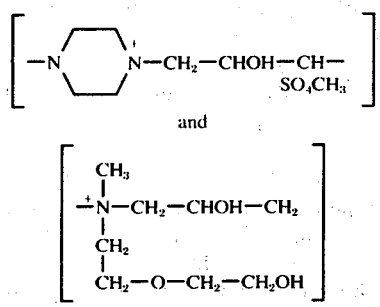

To 1082 g of a 27% aqueous solution of the polymer prepared in Example 48 of which 80% of the sodium chloride has been eliminated by dialysis, and containing 3.37 nitrogen equivalents, there are added with agitation and at a temperature lower than 30° C, 254.5 g (2.02 moles) of dimethyl sulfate. After 3 hours of agitation at this temperature, a 30% solution of the said polymer is produced by the addition of 485 g of water.

The film obtained by evaporation of an aqueous solution of said polymer is hard and slightly sticky.

EXAMPLE 59

Preparation of a polymer quaternized by dimethyl sulfate and constituted by the following two units:

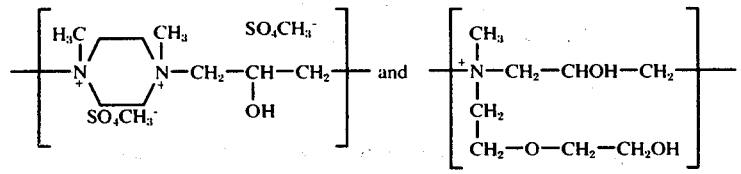

in the proportion of about 80/20.

To a mixture of 141 g (1.64 mole) of piperazine and 42 g (0.4 mole) of diglycolamine dissolved in 300 cc of methanol, there are added with agitation and over a 1 hour period at 20° C, 185 g (2 moles) of epichlorohydrin. The resulting reaction mixture is then heated for 30 minutes at solvent reflux.

There are then added, over a 2 hour period with heating at the reflux of methanol, 360 g (2 moles) of a 30% solution of sodium methylate in methanol. The resulting sodium chloride is eliminated by filtration.

261 g of the above solution containing 0.942 equivalent of nitrogen is heated under reduced pressure to eliminate the methanol. 200 cc of dimethyl-formamide are then added thereto.

To this resulting solution 119 g (0.942 mole) of methyl sulfate are added and the mixture is heated with agitation for 4 hours at 90° C.

By the dropwise addition of this solution in a great excess of acetone, the above polymer in the form of very hygroscopic powder is isolated.

The film obtained by evaporation of an aqueous solution of the said polymer is transparent, hard and not sticky.

EXAMPLES OF USE

Example 60
Anionic shampoo:

| | | |
|---|---:|---|
| Compound of Example 49 | 1 | g |
| Triethanolamine lauryl sulfate | 15 | g |
| Copra diethanolamide | 3 | g |
| Lactic acid, q.s.p. pH 7.4 | | |
| Water, q.s.p. | 100 | g |

Example 61
Anionic shampoo:

| | | |
|---|---:|---|
| Compound of Example 50 | 1.2 | g |
| Disodium sulfosuccinate semi-ester of modified alkanolamide | 10 | g |
| Sodium lauryl ether sulfate condensed with 2.2 moles of ethylene oxide | 15 | g |
| Copra diethanolamide | 4 | g |
| Water, q.s.p. | 100 | g |
| pH = 7 | | |

Example 62
Shampoo:

| | | |
|---|---:|---|
| Compound of Example 51 | 0.75 | g |
| Lauryl alcohol polyoxyethylenated with 12 moles of ethylene oxide | 12 | g |
| Copra diethanolamide | 4 | g |
| Trimethyl cetyl ammonium bromide | 0.5 | g |
| Citric acid, q.s.p. pH 4 | | |
| Water, q.s.p. | 100 | g |

Example 63
Shampoo:

| | | |
|---|---:|---|
| Sodium lauryl ether sulfate condensed with 2.2 moles of ethylene oxide | 10 | g |
| Compound of Example 49 | 1 | g |
| Alkyl imidazoline of the formula | | |

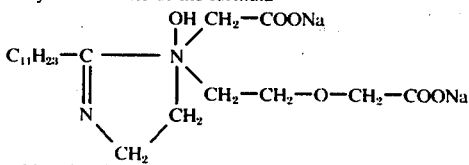

| | | |
|---|---:|---|
| sold under the tradename "Miranol C2M" | 2 | g |
| Copra monoethanolamide | 1.5 | g |
| Lactic acid, q.s.p. pH 7.5 | | |
| Water, q.s.p. | 100 | g |

Example 64
Shampoo:

| | | |
|---|---:|---|
| Compound of Example 50 | 1.5 | g |
| Lauryl alcohol polyoxyethylenated with 12 moles of ethylene oxide | 8 | g |
| Sodium salt of N-(N',N'-diethylamino propyl)$N^2$-dodecyl asparagine | 4 | g |
| Copra diethanolamide | 2 | g |
| Lactic acid, q.s.p. pH 5 | | |
| Water, q.s.p. | 100 | g |

Example 65
Anionic shampoo:

| | | |
|---|---:|---|
| Compound of Example 48 | 1 | g |
| Triethanolamine lauryl sulfate | 10 | g |
| Sodium lauryl ether sulfate oxyethylenated with 2.2 moles of ethylene oxide | 10 | g |
| Copra diethanolamide | 3 | g |
| Water, q.s.p. | 100 | g |
| pH = 8 | | |

Example 66
Anionic shampoo:

| | | |
|---|---:|---|
| Compound of Example 56 | 1 | g |
| Triethanolamine lauryl sulfate | 10 | g |
| Sodium lauryl ether sulfate oxyethylenated | | |

-continued

| EXAMPLES OF USE | | |
|---|---|---|
| with 2.2 moles of ethylene oxide | 10 | g |
| Copra diethanolamide | 3 | g |
| Water, q.s.p. | 100 | g |
| pH = 7.5 | | |

Example 67
Anionic shampoo:
| Compound of Example 56 | 0.75 | g |
|---|---|---|
| Sodium lauryl ether sulfate oxyethylenated with 2.2 moles of ethylene oxide | 10 | g |
| Oxide of lauryl dimethylamine (sold under the tradename Ammonyx LO) | 2 | g |
| Copra diethanolamide | 2.5 | g |
| Water, q.s.p. | 100 | g |
| pH = 7.5 | | |

Example 68
Cationic shampoo:
| Compound of Example 48 | 1.2 | g |
|---|---|---|
| Lauryl alcohol polyoxyethylenated with 12 moles of ethylene oxide | 12 | g |
| Trimethyl cetyl ammonium bromide (sold under the tradename "Cetavlon") | 1 | g |
| Copra diethanolamide | 2 | g |
| Lactic acid, q.s.p. pH 5 | | |
| Water, q.s.p. | 100 | g |

Example 69
Shampoo:
| Compound of Example 53 | 1.5 | g |
|---|---|---|
| Compound of the formula: $C_{12}H_{25}O-[C_2H_3O(CH_2OH)]_{11}-H$ | 6 | g |
| Compound of the formula: $R-CHOH-CH_2O-[CH_2-CHOH-CH_2O]_{3.5}-H$ where R represents $C_9-C_{12}$ alkyl | 5 | g |
| Oxide of lauryl dimethylamine (sold under the tradename "Ammonyx LO" | 2 | g |
| Lactic acid, q.s.p. pH 4 | | |
| Water, q.s.p. | 100 | g |

Example 70
Shampoo:
| Compound of Example 53 | 1 | g |
|---|---|---|
| Triethanolamine lauryl sulfate | 15 | g |
| Lauryl diethanolamide | 3 | g |
| Water, q.s.p. | 100 | g |
| pH = 7.5 | | |

Example 71
Shampoo:
| Compound of Example 54 | 2 | g |
|---|---|---|
| Sodium lauryl ether sulfate polyoxyethylenated with 2.2 moles of ethylene oxide | 12 | g |
| Copra diethanolamide | 2.5 | g |
| Carboxymethyl cellulose | 0.5 | g |
| Water, q.s.p. | 100 | g |
| pH = 7.3 | | |

Example 72
Shampoo:
| Compond of Example 54 | 1.5 | g |
|---|---|---|
| Compound of the formula: $R-CHOH-CH_2O-[CH_2-CHOH-CH_2-O]_{3.5}-H$ wherein R represents $C_9-C_{12}$ alkyl | 6 | g |
| Lauryl alcohol polyoxyethylenated with 12 moles of ethylene oxide | 5 | g |
| Lactic acid, q.s.p. pH 5 | | |
| Water, q.s.p. | 100 | g |

Example 73
Anionic shampoo:
| Compound of Example 58 | 1.5 | g |
|---|---|---|
| Lauryl myristyl ether sulfate of monoethanolamine oxyethylenatd with 2.2 moles of ethylene oxide | 12 | g |
| Copra diethanolamide | 2.5 | g |
| Water, q.s.p. | 100 | g |
| pH = 8 | | |

Example 74
Anionic shampoo:
| Compound of Example 58 | 1 | g |
|---|---|---|
| Oxide of lauryl dimethylamine having the formula:<br>$C_{12}H_{25}-\underset{\underset{CH_3}{\mid}}{\overset{\overset{CH_3}{\mid}}{N}}\rightarrow O$ | 1.5 | g |
| Diethanolamides of fatty acids of copra | 2 | g |

EXAMPLES OF USE

| | | |
|---|---|---|
| Lauryl myristyl ether sulfate of sodium oxyethylenated with 2.2 moles of ethylene oxide | 8.5 | g |
| Water, q.s.p. | 100 | g |
| pH = 7.5 | | |

Example 75
Cationic shampoo:

| | | |
|---|---|---|
| Compound of Example 58 | 2 | g |
| Lauryl alcohol oxyethylenated with 12 moles of ethylene oxide | 10 | g |
| Diethanolamides of fatty acids of copra | 3 | g |
| Oxide of lauryl dimethylamine | 2.5 | g |
| Water, q.s.p. | 100 | g |
| pH = 5 | | |

Example 76
Anionic shampoo:

| | | |
|---|---|---|
| Compound prepared according to example 35 | 2 | g |
| $C_{12}H_5O-(C_2H_3O(CH_2OH))_{\overline{n}}H$ n represents an average statistical value of 4 | 7 | g |
| Lauryl alcohol oxyethylenated with 12 moles of ethylene oxide | 7 | g |
| Lauryl diethanolamide | 3 | g |
| water q.s.p. | 100 | g |
| pH = 7 | | |

Example 77
Nonionic shampoo:

| | | |
|---|---|---|
| Compound prepared according to example 35 | 1.5 | g |
| Lauryl alcohol oxyethylenated with 12 moles of ethylene oxide | 7 | g |
| Alkyl ($C_{12}$–$C_{18}$) dimethylammonio acetate sold under the trademark "Dehyton A B 30" | 10 | g |
| Lauryl diethanolamide | 3 | g |
| Lactic acid q.s.p. pH 5 | | |
| Water q.s.p. | 100 | g |

Example 78
Nonionic shampoo:

| | | |
|---|---|---|
| Compound prepared according to the example 41 | 1 | g |
| $C_{12}H_{25}O-(C_2H_3O(CH_2OH))_{\overline{n}}H$ n represents an average statistical value of 4 | 7 | g |
| Lauryl alcohol oxyethylenated with 12 moles of ethylene oxide | 7 | g |
| Lauryl diethanolamide | 3 | g |
| Water q.s.p. | 100 | g |
| pH = 7 | | |

Example 79
Nonionic shampoo:

| | | |
|---|---|---|
| Compound prepared according to example 41 | 1.3 | g |
| Alkyl ($C_{12}$–$C_{18}$) dimethylammonio acetate sold under the trademark "Dehyton A B 30" | 10 | g |
| Lauryl alcohol oxyethylenated with 12 moles of ethylene oxide | 7 | g |
| Lauryl diethanolamide | 3 | g |
| Lactic acid q.s.p. pH = 5 | | |
| Water q.s.p. | 100 | g |

What is claimed is:

1. A cosmetic composition for conditioning the hair comprising a solution in a solvent selected from the group consisting of water and water-lower alkanol, of a member selected from the group consisting of 1. a film-forming cationic polymer having a molecular weight of about 1,000 to 15,000 and having the formula

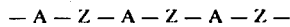

wherein A represents

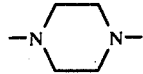

and Z represents B and B' wherein B and B' each independently represent a bivalent radical selected from the group consisting of (i) hydroxypropylene, (ii) alkylene having up to 5 carbon atoms inclusive and interrupted by 1 – 2 members selected from the group consisting of —CONH,

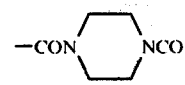

and —CONH—$R_1$—NHCO— wherein $R_1$ represents alkylene having up to 6 carbon atoms, (iii) hydroxy alkylene wherein the alkylene moiety has up to 6 carbon atoms inclusive and interrupted by a member selected from the group consisting of alkylamine wherein the alkyl moiety has 8–18 carbon atoms, benzylamine, oleylamine and oxygen, and (iv) hydroxy propyl-piperazinyl-hydroxy propyl, 2. the quaternary ammonium salt of the cationic polymer in (1) and 3. the oxidation product of the cationic polymer in (1), said member being present in an amount of about 0.1 to 5 percent by weight of said composition.

2. The composition of claim 1, characterized by the fact that it is in the form of a cream.

3. The composition according to claim 1 having a pH between 3 and 11.

4. The composition of claim 1 in the form of a shampoo which also includes an anionic, cationic, nonionic or amphoteric surfactant.

5. The composition according to claim 1 wherein said cationic polymer has a molecular weight less than 15,000.

6. A method of conditioning the hair comprising applying to said hair an effective amount of the composition of claim 1.

7. A cosmetic composition for conditioning the hair comprising a cosmetic carrier and a member selected from the group consisting of
   1. a film-forming cationic polymer having a molecular weight of about 1,000 to 15,000 and having the formula — A — Z — wherein unit A represents

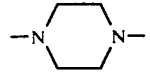

and Z represents unit $B'_1$ or both units $B_1$ and $B'_1$ with the proviso that at least one unit $B'_1$ is present;

$B_1$ represents a bivalent straight or branched chain alkylene having up to 7 carbon atoms in the principal chain substituted by a hydroxy group; and $B'_1$ is a bivalent straight or branched chain alkylene having up to 7 carbon atoms in the principal chain, unsubstituted or substituted by at least one hydroxy group and interrupted by at least one nitrogen atom, the said nitrogen atom being substituted by alkyl having 1–4 carbon atoms and optionally being interrupted by oxygen but necessarily carrying a substituent selected from the group consisting of hydroxy, carboxyl and mixture thereof;

2. the quaternary ammonium salt of the polymer of (1); and 3. the oxidation product of the polymer of (1), said polymer being present in an amount of about 0.1 to 5 percent by weight of said composition.

8. The composition of claim 7 wherein $B_1$ represents hydroxy alkylene, $B'_1$ represents polyhydroxy alkylene interrupted by a nitrogen atom substituted by a carboxymethyl, 2-β-hydroxyethyl, 1,3-di-hydroxy-2-methyl-propyl-2 or 1-hydroxy-2-methyl propyl-2 group.

9. The composition of claim 8 wherein $B_1$ is 2-hydroxy propane-1,3-diyl.

10. The composition of claim 7 wherein said carrier is water, a hydroalcoholic solvent, alcohol, a cream, a paste or a gel.

11. The composition of claim 7 having a pH between 3 and 11.

12. The composition of claim 7 in the form of a shampoo which also includes an anionic, cationic, nonionic or amphoteric surface active agent.

13. The composition of claim 7 which also includes a thickening agent, an opacifier, a sequestrant, a superfatting agent, a softener, a germicide, a preservative, a gum, a perfume, a dye or a cosmetic film-forming resin other than polymer — A — Z —.

14. A cosmetic composition for conditioning the hair comprising a cosmetic carrier and a film-forming polymer having a molecular weight of about 1,000 to 15,000 and having the formula — A' — Z' — wherein unit A' represents a mixture of

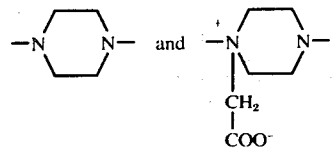

groups and Z' represents a unit selected from the group consisting of B, B', $B_1$, $B'_1$ or one of said B, B', $B_1$ or $B'_1$ units quaternized with a member selected from the group consisting chloracetic acid and sodium chloroacetate when said units carry at least one basic nitrogen atom wherein said quaternized nitrogen has the formula

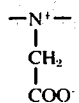

B and B' each independently represent a bivalent straight or branched chain alkylene having up to 7 carbon atoms in the principal chain, unsubstituted or substituted by at least one hydroxy group and optionally by a further substituent selected from the group consisting of oxygen, nitrogen, sulfur, 1–3 aromatic rings and 1–3 heterocyclic rings, the said oxygen, nitrogen and sulfur of said further substituent being in the form of a corresponding ether, thioether, sulfoxide, sulfone, sulfonium, amine, alkylamine, alkenylamine, benzylamine, amine oxide, amide, imide, alcohol, ester or urethane group;

$B_1$ represents a bivalent straight or branched alkylene having up to 7 carbon atoms in the principal chain substituted by hydroxy; and $B'_1$ represents a bivalent straight or branched chain alkylene having up to 7 carbon atoms in the principal chain, unsubstituted or substituted by at least one hydroxy group and interrupted by at least one nitrogen atom, the said nitrogen atom being substituted by alkyl having 1–4 carbon atoms and optionally being interrupted by oxygen but necessarily carrying a substituent selected from the group consisting of hydroxy, carboxyl and mixtures thereof.

said polymer being present in an amount of about 0.1 to 5 percent by weight of said composition.

15. The composition of claim 14, in the form of a shampoo which also includes an anionic, cationic, nonionic or amphoteric surface active agent.

16. A film-forming cationic polymer selected from the group consisting of
   1. a polymer having a molecular weight of about 1,000 to 15,000 and having the formula

wherein A represents

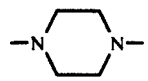

and Z represents B and B' wherein B and B' each independently represent a bivalent radical selected from the group consisting of (i) hydroxypropylene, (ii) alkylene having up to 5 carbon atoms inclusive and interrupted by 1-2 members selected from the group consisting of —CONH,

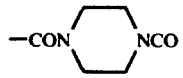

and —CONH—$R_1$—NHCO— wherein $R_1$ represents alkylene having up to 6 carbon atoms, (iii) hydroxy alkylene wherein the alkylene moiety has up to 6 carbon atoms inclusive and interrupted by a member selected from the group consisting of alkylamine wherein the alkyl moiety has 8–18 carbon atoms, benzylamine, oleylamine and oxygen, and (iv) hydroxypropyl-piperazinylhydroxy propyl;

2. the quaternary ammonium salt of the cationic polymer in (1) and
3. the oxidation product of the cationic polymer in (1).

17. A film-forming cationic polymer selected from the group consisting of
 1. a polymer having a molecular weight of about 1,000 to 15,000 and having the formula — A — Z — wherein unit A represents

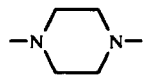

and unit Z represents unit $B'_1$ or both units $B_1$ and $B'_1$, with the proviso that at least one $B'_1$ unit is present therein,
$B_1$ represents a bivalent straight or branched chain alkylene having up to 7 carbon atoms in the principal chain substituted by a hydroxy group; and
$B'_1$ is a bivalent straight or branched chain alkylene having up to 7 carbon atoms in the principal chain, unsubstituted or substituted by at least one hydroxy group and interrupted by at least one nitrogen atom, the said nitrogen atom being substituted by alkyl having 1-4 carbon atoms and optionally being interrupted by oxygen but necessarily carrying a substituent selected from the group consisting of hydroxy, carboxyl and mixtures thereof;
 2. the quaternary ammonium salt of the polymer of (1); and
 3. the oxidation product of the polymer of (1).

18. The polymer of claim 17 wherein $B_1$ is 2-hydroxy propane-1,3-diyl.

19. The polymer of claim 17 wherein the said nitrogen atom is substituted by a member selected from the group consisting of carboxy methyl, 2-$\beta$-hydroxethoxy ethyl, 1,3-dihydroxy-2-methyl-propyl-2 and 1-hydroxy-2-methyl-propyl-2.

20. A film-forming polymer having a molecular weight of about 1,000 to 15,000 and having the formula — A' — Z'— wherein unit A' represents a mixture of

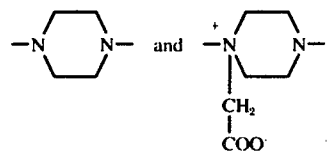

groups and Z' represents a unit selected from the group consisting of B, B', $B_1$ and $B'_1$ and B', or one of said B, B', $B_1$ and $B'_1$ units quaternized with a member selected from the group consisting of chloroacetic acid and sodium chloroacetate when said units carry at least one basic nitrogen atom whereby said quaternized nitrogen has the formula

B and B' each independently represent a bivalent straight or branched chain alkylene having up to 7 carbon atoms in the principal chain, unsubstituted or substituted by at least one hydroxy group and optionally by a further substituent selected from the group consisting of oxygen, nitrogen, sulphur, 1–3 aromatic rings and 1–3 heterocylic rings, the said oxygen, nitrogen and sulfur of said further substituent being in the form of a corresponding ether, thioether, sulfoxide, sulfone, sulfonium, amine, alkylamine, alkenylamine, benzylamine, amine oxide, amide, imide, alcohol, ester or urethane group;
$B_1$ represents a bivalent straight or branched alkylene having up to 7 carbon atoms in the principal chain substituted by hydroxy; and
$B'_1$ represents a bivalent straight or branched chain alkylene having up to 7 carbon atoms in the principal chain, unsubstituted or substituted by at least one hydroxy group and interrupted by at least one nitrogen atom, the said nitrogen atom being substituted by alkyl having 1–4 carbon atoms and optionally being interrupted by oxygen but necessarily carrying a substituent selected from the group consisting of hydroxy, carboxyl and mixtures thereof.

* * * * *

UNITED STATES PATENT OFFICE
CERTIFICATE OF CORRECTION

Patent No. 4,013,787　　　　　　　　Dated　March 22, 1977

Inventor(s) Guy Vanlerberghe and Henri Sebag

It is certified that error appears in the above-identified patent and that said Letters Patent are hereby corrected as shown below:

In the Heading:

Change "Guy Varlerberghe" to
--Guy Vanlerberghe--.

Signed and Sealed this

Twenty-ninth Day of November 1977

[SEAL]

*Attest:*

RUTH C. MASON　　　　　　LUTRELLE F. PARKER
*Attesting Officer*　　　　*Acting Commissioner of Patents and Trademarks*